United States Patent
Lindsey et al.

(10) Patent No.: US 12,427,028 B2
(45) Date of Patent: Sep. 30, 2025

(54) THREADED IMPLANTS AND METHODS OF USE ACROSS BONE SEGMENTS

(71) Applicant: SI-Bone Inc., Santa Clara, CA (US)

(72) Inventors: Derek P. Lindsey, San Jose, CA (US);
Paul Sand, Redwood City, CA (US);
Bret W. Schneider, San Jose, CA (US);
Scott A. Yerby, Montara, CA (US);
Nikolas F. Kerr, Milpitas, CA (US);
Regina Macbarb, Carlsbad, CA (US)

(73) Assignee: SI-Bone Inc., Santa Clara, CA (US)

( * ) Notice: Subject to any disclaimer, the term of this patent is extended or adjusted under 35 U.S.C. 154(b) by 0 days.

(21) Appl. No.: 18/066,872

(22) Filed: Dec. 15, 2022

(65) Prior Publication Data

US 2023/0210667 A1    Jul. 6, 2023

Related U.S. Application Data

(63) Continuation of application No. 16/368,686, filed on Mar. 28, 2019, now abandoned.
(Continued)

(51) Int. Cl.
*A61F 2/30* (2006.01)
*A61B 17/80* (2006.01)
(Continued)

(52) U.S. Cl.
CPC .......... *A61F 2/30988* (2013.01); *A61B 17/80* (2013.01); *A61F 2/28* (2013.01); *A61F 2/30* (2013.01); *A61F 2/4603* (2013.01); *A61F 2002/2835* (2013.01); *A61F 2002/30011* (2013.01); *A61F 2002/30156* (2013.01); *A61F 2002/30289* (2013.01);
(Continued)

(58) Field of Classification Search
CPC . A61F 2002/30851; A61F 2002/30858; A61B 17/869
See application file for complete search history.

(56) References Cited

U.S. PATENT DOCUMENTS

| 1,951,278 | A | 3/1934 | Ericsson |
| 2,136,471 | A | 11/1938 | Schneider |

(Continued)

FOREIGN PATENT DOCUMENTS

| CN | 1128944 A | 8/1996 |
| CN | 1190882 A | 8/1998 |

(Continued)

OTHER PUBLICATIONS

ACUMED; Acutrak Headless Compressioin Screw (product information); 12 pgs; © 2005; retrieved Sep. 25, 2014 from http://www.rcsed.ac.uk/fellows/lvanrensburg/classification/surgtech/acumed/manuals/acutrak-brochure%200311.pdf.
(Continued)

*Primary Examiner* — Javier G Blanco
(74) *Attorney, Agent, or Firm* — Shay Glenn LLP

(57) ABSTRACT

A threaded implant can be provided with an elongated main body having external threads configured to thread into bone, and an internal support structure located within the external threads. The internal support structure has a helical arrangement that extends in an opposite direction to the external threads. Other threaded implants and methods are also disclosed.

8 Claims, 22 Drawing Sheets

Related U.S. Application Data

(60) Provisional application No. 62/649,466, filed on Mar. 28, 2018.

(51) Int. Cl.
*A61F 2/28* (2006.01)
*A61F 2/46* (2006.01)

(52) U.S. Cl.
CPC .............. *A61F 2002/30405* (2013.01); *A61F 2002/30622* (2013.01); *A61F 2002/30784* (2013.01); *A61F 2002/30858* (2013.01); *A61F 2002/30868* (2013.01); *A61F 2002/30995* (2013.01)

(56) References Cited

U.S. PATENT DOCUMENTS

| | | |
|---|---|---|
| 2,243,717 A | 5/1941 | Moreira |
| 2,414,882 A | 1/1947 | Longfellow |
| 2,562,419 A | 7/1951 | Ferris |
| 2,675,801 A | 4/1954 | Bambara et al. |
| 2,697,433 A | 12/1954 | Zehnder |
| 3,076,453 A | 2/1963 | Tronzo |
| 3,506,982 A | 4/1970 | Steffee |
| 3,694,821 A | 10/1972 | Moritz |
| 3,709,218 A | 1/1973 | Halloran |
| 3,744,488 A | 7/1973 | Cox |
| 4,059,115 A | 11/1977 | Jumashev et al. |
| 4,156,943 A | 6/1979 | Collier |
| 4,197,645 A | 4/1980 | Scheicher |
| 4,292,964 A | 10/1981 | Ulrich |
| 4,341,206 A | 7/1982 | Perrett et al. |
| 4,344,190 A | 8/1982 | Lee et al. |
| 4,399,813 A | 8/1983 | Barber |
| 4,423,721 A | 1/1984 | Otte et al. |
| 4,475,545 A | 10/1984 | Ender |
| 4,501,269 A | 2/1985 | Bagby |
| 4,569,338 A | 2/1986 | Edwards |
| 4,612,918 A | 9/1986 | Slocum |
| 4,622,959 A | 11/1986 | Marcus |
| 4,630,601 A | 12/1986 | Harder et al. |
| 4,638,799 A | 1/1987 | Moore |
| 4,657,550 A | 4/1987 | Daher |
| 4,743,256 A | 5/1988 | Brantigan |
| 4,773,402 A | 9/1988 | Asher et al. |
| 4,787,378 A | 11/1988 | Sodhi |
| 4,790,303 A | 12/1988 | Steffee |
| 4,834,757 A | 5/1989 | Brantigan |
| 4,846,162 A | 7/1989 | Moehring |
| 4,877,019 A | 10/1989 | Vives |
| 4,878,915 A | 11/1989 | Brantigan |
| 4,898,186 A | 2/1990 | Ikada et al. |
| 4,904,261 A | 2/1990 | Dove et al. |
| 4,950,270 A | 8/1990 | Bowman et al. |
| 4,961,740 A | 10/1990 | Ray et al. |
| 4,969,888 A | 11/1990 | Scholten et al. |
| 4,981,481 A | 1/1991 | Kranz et al. |
| 5,034,011 A | 7/1991 | Howland |
| 5,034,013 A | 7/1991 | Kyle et al. |
| 5,035,697 A | 7/1991 | Frigg |
| 5,041,118 A | 8/1991 | Wasilewski |
| 5,053,035 A | 10/1991 | McLaren |
| 5,059,193 A | 10/1991 | Kuslich |
| 5,066,296 A | 11/1991 | Chapman et al. |
| 5,098,434 A | 3/1992 | Serbousek |
| 5,102,414 A | 4/1992 | Kirsch |
| 5,108,397 A | 4/1992 | White |
| 5,122,141 A | 6/1992 | Simpson et al. |
| 5,139,498 A | 8/1992 | Astudillo Ley |
| 5,139,500 A | 8/1992 | Schwartz |
| 5,147,367 A | 9/1992 | Ellis |
| 5,147,402 A | 9/1992 | Bohler et al. |
| 5,190,551 A | 3/1993 | Chin et al. |
| 5,197,961 A | 3/1993 | Castle |
| 5,242,444 A | 9/1993 | MacMillan |
| 5,298,254 A | 3/1994 | Prewett et al. |
| 5,334,205 A | 8/1994 | Cain |
| 5,380,325 A | 1/1995 | Lahille et al. |
| 5,390,683 A | 2/1995 | Pisharodi |
| 5,433,718 A | 7/1995 | Brinker |
| 5,443,466 A | 8/1995 | Shah |
| 5,458,638 A | 10/1995 | Kuslich et al. |
| 5,470,334 A | 11/1995 | Ross et al. |
| 5,480,402 A | 1/1996 | Kim |
| 5,569,249 A | 10/1996 | James et al. |
| 5,591,235 A | 1/1997 | Kuslich |
| 5,593,409 A | 1/1997 | Michelson |
| 5,607,424 A | 3/1997 | Tropiano |
| 5,609,635 A | 3/1997 | Michelson |
| 5,609,636 A | 3/1997 | Kohrs et al. |
| 5,626,616 A | 5/1997 | Speece |
| 5,643,264 A | 7/1997 | Sherman et al. |
| 5,645,599 A | 7/1997 | Samani |
| 5,658,337 A | 8/1997 | Kohrs et al. |
| 5,667,510 A | 9/1997 | Combs |
| 5,669,909 A | 9/1997 | Zdeblick et al. |
| 5,672,178 A | 9/1997 | Petersen |
| 5,683,391 A | 11/1997 | Boyd |
| 5,709,683 A | 1/1998 | Bagby |
| 5,713,904 A | 2/1998 | Errico et al. |
| 5,716,358 A | 2/1998 | Ochoa et al. |
| 5,725,581 A | 3/1998 | Brånemark |
| 5,743,912 A | 4/1998 | LaHille et al. |
| 5,759,035 A | 6/1998 | Ricci |
| 5,766,174 A | 6/1998 | Perry |
| 5,766,252 A | 6/1998 | Henry et al. |
| 5,766,261 A | 6/1998 | Neal et al. |
| 5,788,699 A | 8/1998 | Bobst et al. |
| 5,800,440 A | 9/1998 | Stead |
| 5,868,749 A | 2/1999 | Reed |
| 5,897,556 A | 4/1999 | Drewry et al. |
| 5,928,239 A | 7/1999 | Mirza |
| 5,941,885 A | 8/1999 | Jackson |
| 5,961,522 A | 10/1999 | Mehdizadeh |
| 5,961,554 A | 10/1999 | Janson et al. |
| 6,010,507 A | 1/2000 | Rudloff |
| 6,015,409 A | 1/2000 | Jackson |
| 6,030,162 A | 2/2000 | Huebner et al. |
| 6,053,916 A | 4/2000 | Moore |
| 6,056,749 A | 5/2000 | Kuslich |
| 6,066,175 A | 5/2000 | Henderson et al. |
| 6,086,589 A | 7/2000 | Kuslich et al. |
| 6,096,080 A | 8/2000 | Nicholson et al. |
| 6,120,292 A | 9/2000 | Buser et al. |
| 6,120,504 A | 9/2000 | Brumback et al. |
| 6,129,730 A | 10/2000 | Bono et al. |
| 6,143,031 A | 11/2000 | Knothe et al. |
| 6,197,062 B1 | 3/2001 | Fenlin |
| 6,206,924 B1 | 3/2001 | Timm |
| 6,210,442 B1 | 4/2001 | Wing et al. |
| 6,214,049 B1 | 4/2001 | Gayer et al. |
| 6,221,074 B1 | 4/2001 | Cole et al. |
| 6,224,607 B1 | 5/2001 | Michelson |
| 6,241,732 B1 | 6/2001 | Overaker et al. |
| 6,264,657 B1 | 7/2001 | Urbahns et al. |
| 6,270,528 B1 | 8/2001 | McKay |
| 6,287,343 B1 | 9/2001 | Kuslich et al. |
| 6,302,885 B1 | 10/2001 | Essiger |
| 6,302,914 B1 | 10/2001 | Michelson |
| 6,306,140 B1 | 10/2001 | Siddiqui |
| 6,319,253 B1 | 11/2001 | Ackeret et al. |
| 6,406,498 B1 | 6/2002 | Tormala et al. |
| 6,409,768 B1 | 6/2002 | Tepic et al. |
| 6,436,139 B1 | 8/2002 | Shapiro et al. |
| 6,451,020 B1 | 9/2002 | Zucherman et al. |
| 6,471,707 B1 | 10/2002 | Miller et al. |
| 6,485,518 B1 | 11/2002 | Cornwall et al. |
| 6,497,707 B1 | 12/2002 | Bowman et al. |
| 6,517,541 B1 | 2/2003 | Sesic |
| 6,520,969 B2 | 2/2003 | Lambrecht et al. |
| 6,524,314 B1 | 2/2003 | Dean et al. |
| 6,527,775 B1 | 3/2003 | Warburton |
| 6,551,343 B1 | 4/2003 | Törmälä et al. |

(56) References Cited

U.S. PATENT DOCUMENTS

| | | |
|---|---|---|
| 6,556,857 B1 | 4/2003 | Estes et al. |
| 6,558,386 B1 | 5/2003 | Cragg |
| 6,565,566 B1 | 5/2003 | Wagner et al. |
| 6,575,899 B1 | 6/2003 | Foley et al. |
| 6,575,991 B1 | 6/2003 | Chesbrough et al. |
| 6,579,293 B1 | 6/2003 | Chandran |
| 6,582,431 B1 | 6/2003 | Ray |
| 6,582,467 B1 | 6/2003 | Teitelbaum et al. |
| 6,595,998 B2 | 7/2003 | Johnson et al. |
| 6,602,293 B1 | 8/2003 | Biermann et al. |
| 6,605,090 B1 | 8/2003 | Trieu et al. |
| 6,607,530 B1 | 8/2003 | Carl et al. |
| 6,620,163 B1 | 9/2003 | Michelson |
| 6,635,059 B2 | 10/2003 | Randall et al. |
| 6,666,868 B2 | 12/2003 | Fallin |
| 6,669,529 B1 | 12/2003 | Scaries |
| 6,673,075 B2 | 1/2004 | Santilli |
| 6,692,501 B2 | 2/2004 | Michelson |
| 6,712,852 B1 | 3/2004 | Chung et al. |
| 6,723,099 B1 | 4/2004 | Goshert |
| 6,723,100 B2 | 4/2004 | Biedermann et al. |
| 6,740,118 B2 | 5/2004 | Elsermann et al. |
| 6,743,257 B2 | 6/2004 | Castro |
| D493,533 S | 7/2004 | Blain |
| 6,793,656 B1 | 9/2004 | Mathews |
| 6,827,740 B1 | 12/2004 | Michelson |
| 6,984,235 B2 | 1/2006 | Huebner |
| 6,989,033 B1 | 1/2006 | Schmidt |
| 6,991,461 B2 | 1/2006 | Gittleman |
| 6,993,406 B1 | 1/2006 | Cesarano et al. |
| 7,018,416 B2 | 3/2006 | Hanson et al. |
| 7,118,579 B2 | 10/2006 | Michelson |
| 7,147,666 B1 | 12/2006 | Grisoni |
| 7,175,663 B1 | 2/2007 | Stone |
| 7,211,085 B2 | 5/2007 | Michelson |
| 7,223,269 B2 | 5/2007 | Chappuis |
| 7,300,439 B2 | 11/2007 | May |
| 7,314,488 B2 | 1/2008 | Reiley |
| 7,335,205 B2 | 2/2008 | Aeschlimann et al. |
| 7,338,500 B2 | 3/2008 | Chappuis |
| 7,396,365 B2 | 7/2008 | Michelson |
| 7,452,359 B1 | 11/2008 | Michelson |
| 7,452,369 B2 | 11/2008 | Barry |
| 7,481,831 B2 | 1/2009 | Bonutti |
| 7,527,649 B1 | 5/2009 | Blain |
| 7,534,254 B1 | 5/2009 | Michelson |
| 7,537,616 B1 | 5/2009 | Branch et al. |
| 7,569,054 B2 | 8/2009 | Michelson |
| 7,569,059 B2 | 8/2009 | Cerundolo |
| 7,601,155 B2 | 10/2009 | Petersen |
| 7,608,097 B2 | 10/2009 | Kyle |
| 7,608,098 B1 | 10/2009 | Stone et al. |
| 7,648,509 B2 | 1/2010 | Stark |
| 7,686,805 B2 | 3/2010 | Michelson |
| 7,699,852 B2 | 4/2010 | Frankel et al. |
| 7,708,761 B2 | 5/2010 | Petersen |
| 7,727,235 B2 | 6/2010 | Contiliano et al. |
| 7,758,646 B2 | 7/2010 | Khandkar et al. |
| 7,780,704 B2 | 8/2010 | Markworth et al. |
| 7,846,162 B2 | 12/2010 | Nelson et al. |
| 7,850,732 B2 | 12/2010 | Heinz |
| 7,857,832 B2 | 12/2010 | Culbert et al. |
| 7,887,565 B2 | 2/2011 | Michelson |
| 7,892,265 B2 | 2/2011 | Perez-Cruet et al. |
| 7,901,439 B2 | 3/2011 | Horton |
| 7,909,832 B2 | 3/2011 | Michelson |
| 7,922,765 B2 | 4/2011 | Reiley |
| 7,942,879 B2 | 5/2011 | Christie et al. |
| 7,951,176 B2 | 5/2011 | Grady et al. |
| 8,052,728 B2 | 11/2011 | Hestad |
| 8,062,365 B2 | 11/2011 | Schwab |
| 8,066,705 B2 | 11/2011 | Michelson |
| 8,066,709 B2 | 11/2011 | Michelson |
| 8,092,505 B2 | 1/2012 | Sommers |
| 8,142,481 B2 | 3/2012 | Warnick |
| 8,202,305 B2 | 6/2012 | Reiley |
| 8,221,499 B2 | 7/2012 | Lazzara et al. |
| 8,257,398 B2 | 9/2012 | Jackson |
| 8,268,099 B2 | 9/2012 | O'Neill et al. |
| 8,308,779 B2 | 11/2012 | Reiley |
| 8,308,783 B2 | 11/2012 | Morris et al. |
| 8,317,862 B2 | 11/2012 | Troger et al. |
| 8,348,950 B2 | 1/2013 | Assell et al. |
| 8,350,186 B2 | 1/2013 | Jones et al. |
| 8,353,932 B2 | 1/2013 | Jackson |
| 8,388,667 B2 | 3/2013 | Reiley et al. |
| 8,394,129 B2 | 3/2013 | Morgenstern Lopez |
| 8,398,635 B2 | 3/2013 | Vaidya |
| 8,398,682 B2 | 3/2013 | Jackson et al. |
| 8,414,648 B2 | 4/2013 | Reiley |
| 8,425,570 B2 | 4/2013 | Reiley |
| 8,430,930 B2 | 4/2013 | Hunt |
| 8,444,693 B2 | 5/2013 | Reiley |
| 8,449,585 B2 | 5/2013 | Wallenstein et al. |
| 8,467,851 B2 | 6/2013 | Mire et al. |
| 8,470,004 B2 | 6/2013 | Reiley |
| 8,475,505 B2 | 7/2013 | Nebosky et al. |
| 8,529,608 B2 | 9/2013 | Terrill et al. |
| 8,597,299 B2 | 12/2013 | Farr et al. |
| 8,608,802 B2 | 12/2013 | Bagga et al. |
| D697,209 S | 1/2014 | Walthall et al. |
| 8,641,737 B2 | 2/2014 | Matthis et al. |
| 8,641,766 B2 | 2/2014 | Donner et al. |
| 8,663,298 B2 | 3/2014 | Keyer et al. |
| 8,663,332 B1 | 3/2014 | To et al. |
| 8,672,986 B2 | 3/2014 | Klaue et al. |
| 8,734,462 B2 | 5/2014 | Reiley et al. |
| 8,778,026 B2 | 7/2014 | Mauldin |
| 8,840,623 B2 | 9/2014 | Reiley |
| 8,840,651 B2 | 9/2014 | Reiley |
| 8,845,693 B2 | 9/2014 | Smith et al. |
| 8,858,601 B2 | 10/2014 | Reiley |
| 8,888,827 B2 | 11/2014 | Harper et al. |
| 8,894,685 B2 | 11/2014 | Mickiewicz et al. |
| 8,920,477 B2 | 12/2014 | Reiley |
| 8,926,670 B2 | 1/2015 | Jackson |
| 8,936,623 B2 | 1/2015 | Jackson |
| 8,945,190 B2 | 2/2015 | Culbert et al. |
| 8,945,193 B2 | 2/2015 | Kirschman |
| 8,951,254 B2 | 2/2015 | Mayer et al. |
| 8,951,293 B2 | 2/2015 | Glazer et al. |
| 8,951,295 B2 | 2/2015 | Matityahu et al. |
| 8,961,571 B2 | 2/2015 | Lee et al. |
| 8,979,911 B2 | 3/2015 | Martineau et al. |
| 8,986,348 B2 | 3/2015 | Reiley |
| RE45,484 E | 4/2015 | Foley et al. |
| 9,039,743 B2 | 5/2015 | Reiley |
| 9,044,321 B2 | 6/2015 | Mauldin et al. |
| 9,060,876 B1 | 6/2015 | To et al. |
| 9,089,371 B1 | 7/2015 | Faulhaber |
| D738,498 S | 9/2015 | Frey et al. |
| 9,131,955 B2 | 9/2015 | Swofford |
| 9,149,286 B1 | 10/2015 | Greenhalgh et al. |
| 9,173,692 B1 | 11/2015 | Kaloostian |
| 9,198,676 B2 | 12/2015 | Pilgeram et al. |
| 9,220,535 B2 | 12/2015 | Röbling et al. |
| 9,314,286 B2 | 4/2016 | Bottlang et al. |
| 9,314,348 B2 | 4/2016 | Emstad |
| 9,358,047 B2 | 6/2016 | Mishra et al. |
| 9,358,057 B1 | 6/2016 | Whipple et al. |
| 9,375,243 B1 | 6/2016 | Vestgaarden |
| 9,375,323 B2 | 6/2016 | Reiley |
| 9,445,852 B2 | 9/2016 | Sweeney |
| 9,451,999 B2 | 9/2016 | Simpson et al. |
| 9,452,065 B1 | 9/2016 | Lawson |
| 9,486,264 B2 | 11/2016 | Reiley et al. |
| 9,492,201 B2 | 11/2016 | Reiley |
| 9,498,264 B2 | 11/2016 | Harshman et al. |
| 9,510,872 B2 | 12/2016 | Donner et al. |
| 9,517,095 B2 | 12/2016 | Vaidya |
| 9,526,548 B2 | 12/2016 | Asfora |
| 9,554,909 B2 | 1/2017 | Donner |
| 9,561,063 B2 | 2/2017 | Reiley |
| 9,566,100 B2 | 2/2017 | Asfora |

(56) References Cited

U.S. PATENT DOCUMENTS

| | | |
|---|---|---|
| 9,603,613 B2 | 3/2017 | Schoenefeld et al. |
| 9,603,644 B2 | 3/2017 | Sweeney |
| D783,821 S | 4/2017 | Folsom et al. |
| 9,615,856 B2 | 4/2017 | Arnett et al. |
| 9,622,783 B2 | 4/2017 | Reiley et al. |
| 9,655,656 B2 | 5/2017 | Whipple |
| 9,662,124 B2 | 5/2017 | Assell et al. |
| 9,662,128 B2 | 5/2017 | Reiley |
| 9,662,157 B2 | 5/2017 | Schneider et al. |
| 9,662,158 B2 | 5/2017 | Reiley |
| 9,675,394 B2 | 6/2017 | Reiley |
| 9,743,969 B2 | 8/2017 | Reiley |
| 9,757,154 B2 | 9/2017 | Donner et al. |
| 9,763,695 B2 | 9/2017 | Mirda |
| 9,763,802 B2 | 9/2017 | Baynham |
| 9,775,648 B2 | 10/2017 | Greenberg et al. |
| 9,788,866 B2 | 10/2017 | Jackson |
| 9,808,292 B2 | 11/2017 | Jackson |
| 9,808,298 B2 | 11/2017 | Stroncek et al. |
| 9,808,299 B2 | 11/2017 | Goel et al. |
| 9,808,337 B2 | 11/2017 | Housman et al. |
| 9,820,789 B2 | 11/2017 | Reiley |
| 9,826,986 B2 | 11/2017 | Donner et al. |
| 9,833,321 B2 | 12/2017 | Rindal et al. |
| 9,839,448 B2 | 12/2017 | Reckling et al. |
| 9,848,889 B2 | 12/2017 | Taylor et al. |
| 9,848,892 B2 | 12/2017 | Biedermann et al. |
| 9,883,874 B1 | 2/2018 | Vestgaarden |
| 9,888,911 B2 | 2/2018 | Siegal |
| 9,936,983 B2 | 4/2018 | Mesiwala et al. |
| 9,949,776 B2 | 4/2018 | Mobasser et al. |
| 9,949,843 B2 | 4/2018 | Reiley et al. |
| D816,843 S | 5/2018 | Lewis |
| 9,956,013 B2 | 5/2018 | Reiley et al. |
| 9,993,276 B2 | 6/2018 | Russell |
| 9,993,277 B2 | 6/2018 | Krinke et al. |
| 9,999,449 B2 | 6/2018 | Bonutti |
| 10,004,547 B2 | 6/2018 | Reiley |
| 10,034,676 B2 | 7/2018 | Donner |
| 10,058,430 B2 | 8/2018 | Donner et al. |
| 10,064,670 B2 | 9/2018 | Mootien et al. |
| D831,828 S | 10/2018 | Horton et al. |
| 10,166,022 B2 | 1/2019 | Early et al. |
| 10,166,033 B2 | 1/2019 | Reiley et al. |
| 10,179,014 B1 | 1/2019 | Menmuir et al. |
| 10,188,403 B2 | 1/2019 | Mirochinik et al. |
| 10,188,432 B2 | 1/2019 | Jackson et al. |
| 10,188,442 B2 | 1/2019 | Mazel |
| 10,194,951 B2 | 2/2019 | Jackson et al. |
| 10,194,962 B2 | 2/2019 | Schneider et al. |
| 10,201,427 B2 | 2/2019 | Mauldin et al. |
| 10,219,841 B1 | 3/2019 | Compton et al. |
| 10,219,885 B2 | 3/2019 | Mamo et al. |
| D846,977 S | 4/2019 | Williams et al. |
| D847,336 S | 4/2019 | Asfora et al. |
| 10,245,044 B2 | 4/2019 | Petersen |
| 10,245,076 B2 | 4/2019 | Fitzpatrick |
| 10,245,087 B2 | 4/2019 | Donner et al. |
| 10,258,380 B2 | 4/2019 | Sinha |
| 10,258,393 B2 | 4/2019 | Caploon et al. |
| 10,258,394 B2 | 4/2019 | Harshman et al. |
| 10,271,882 B2 | 4/2019 | Biedermann et al. |
| D847,994 S | 5/2019 | Asfora et al. |
| 10,278,737 B2 | 5/2019 | Smith |
| 10,285,745 B2 | 5/2019 | Cummins et al. |
| 10,292,778 B2 | 5/2019 | Kostrzewski et al. |
| D850,616 S | 6/2019 | Asfora et al. |
| 10,314,631 B2 | 6/2019 | Gonzalez Blohm et al. |
| 10,321,937 B2 | 6/2019 | Cormier et al. |
| 10,321,945 B2 | 6/2019 | Schifano et al. |
| 10,335,200 B2 | 7/2019 | Jackson |
| 10,335,202 B2 | 7/2019 | Ziolo et al. |
| 10,335,204 B2 | 7/2019 | Matthis et al. |
| 10,335,206 B2 | 7/2019 | Nichols et al. |
| 10,335,211 B2 | 7/2019 | Chan et al. |
| 10,335,212 B2 | 7/2019 | Paolino et al. |
| 10,335,216 B2 | 7/2019 | Mari et al. |
| 10,335,217 B2 | 7/2019 | Lindner |
| 10,342,586 B2 | 7/2019 | Schneider |
| 10,349,983 B2 | 7/2019 | Purcell et al. |
| 10,349,986 B2 | 7/2019 | Wall et al. |
| 10,357,287 B2 | 7/2019 | Schlaepfer et al. |
| 10,363,070 B2 | 7/2019 | Jackson et al. |
| 10,363,073 B2 | 7/2019 | Raina et al. |
| 10,363,140 B2 | 7/2019 | Mauldin et al. |
| 10,363,143 B2 | 7/2019 | Neubardt |
| 10,368,919 B2 | 8/2019 | Pham et al. |
| 10,413,332 B2 | 9/2019 | Schumacher et al. |
| 10,426,533 B2 | 10/2019 | Mauldin et al. |
| 10,426,539 B2 | 10/2019 | Schifano et al. |
| 10,433,880 B2 | 10/2019 | Donner et al. |
| 10,441,319 B2 | 10/2019 | Jackson et al. |
| 10,456,268 B2 | 10/2019 | Mercier et al. |
| 10,463,402 B2 | 11/2019 | Biester et al. |
| 10,478,227 B2 | 11/2019 | Leff et al. |
| 10,485,596 B2 | 11/2019 | Koller et al. |
| 10,492,841 B2 | 12/2019 | Hartdegen et al. |
| 10,492,921 B2 | 12/2019 | McShane, III et al. |
| 10,517,734 B2 | 12/2019 | Donner |
| 10,531,898 B2 | 1/2020 | Boulot |
| 10,531,904 B2 | 1/2020 | Kolb |
| 10,537,340 B2 | 1/2020 | Mirochinik et al. |
| D875,931 S | 2/2020 | Asfora et al. |
| 10,555,758 B2 | 2/2020 | Magee et al. |
| 10,588,676 B2 | 3/2020 | Kang et al. |
| 10,588,677 B2 | 3/2020 | McDonnell |
| 10,595,917 B2 | 3/2020 | Loftus |
| 10,596,003 B2 | 3/2020 | Donner et al. |
| 10,603,054 B2 | 3/2020 | Asfora et al. |
| 10,603,055 B2 | 3/2020 | Donner et al. |
| 10,603,087 B2 | 3/2020 | Brenzel et al. |
| 10,603,176 B2 | 3/2020 | Arnold et al. |
| 10,610,275 B2 | 4/2020 | Brianza |
| 10,610,276 B2 | 4/2020 | Lutz |
| 10,610,370 B2 | 4/2020 | Baynham |
| 10,610,728 B2 | 4/2020 | Fano et al. |
| 10,617,453 B2 | 4/2020 | Beckett et al. |
| 10,653,454 B2 | 5/2020 | Frey et al. |
| 10,653,455 B2 | 5/2020 | Lehman et al. |
| 10,653,544 B2 | 5/2020 | Forsell |
| 10,660,657 B2 | 5/2020 | Slobitker et al. |
| 10,660,679 B2 | 5/2020 | Kang et al. |
| 10,660,684 B2 | 5/2020 | Kang et al. |
| 10,667,923 B2 | 6/2020 | Sullivan et al. |
| 10,682,131 B2 | 6/2020 | Fallin et al. |
| 10,682,150 B2 | 6/2020 | Stark |
| 10,682,437 B2 | 6/2020 | Roth |
| 10,709,570 B2 | 7/2020 | Stauffer et al. |
| 10,711,334 B2 | 7/2020 | Patel et al. |
| 10,729,475 B2 | 8/2020 | Childs |
| 10,729,482 B2 | 8/2020 | Fantigrossi et al. |
| 10,743,995 B2 | 8/2020 | Fallin et al. |
| D895,111 S | 9/2020 | Frey et al. |
| 10,758,283 B2 | 9/2020 | Frey et al. |
| 10,758,285 B2 | 9/2020 | Geist et al. |
| 10,792,074 B2 | 10/2020 | Jackson |
| 10,799,277 B2 | 10/2020 | Kulper et al. |
| 10,799,367 B2 | 10/2020 | Vrionis et al. |
| 10,806,597 B2 | 10/2020 | Sournac et al. |
| 10,842,511 B2 | 11/2020 | Patel et al. |
| 10,842,634 B2 | 11/2020 | Pasini et al. |
| D904,615 S | 12/2020 | Asfora et al. |
| D905,232 S | 12/2020 | Schifano et al. |
| 10,856,922 B2 | 12/2020 | Loke et al. |
| 10,864,029 B2 | 12/2020 | Redmond et al. |
| 10,898,333 B2 | 1/2021 | Cordaro |
| 10,905,472 B2 | 2/2021 | Mari et al. |
| 10,912,654 B2 | 2/2021 | Scheland |
| 10,932,838 B2 | 3/2021 | Mehl et al. |
| 10,939,944 B2 | 3/2021 | Wapner et al. |
| 10,940,008 B2 | 3/2021 | Patel |
| 10,959,758 B2 | 3/2021 | Mesiwala et al. |
| 10,959,830 B2 | 3/2021 | Williams et al. |
| 10,987,142 B2 | 4/2021 | Poelstra et al. |

(56) References Cited

U.S. PATENT DOCUMENTS

| | | |
|---|---|---|
| 10,993,754 B2 | 5/2021 | Kuntz et al. |
| 10,993,757 B2 | 5/2021 | Schifano et al. |
| 11,000,325 B2 | 5/2021 | Sommers et al. |
| 11,006,985 B2 | 5/2021 | Caploon et al. |
| D921,898 S | 6/2021 | Schifano et al. |
| D922,568 S | 6/2021 | Schifano et al. |
| 11,033,309 B2 | 6/2021 | Zadeh |
| 11,051,856 B2 | 7/2021 | Jackson |
| 11,052,229 B2 | 7/2021 | Althoff et al. |
| 11,058,443 B2 | 7/2021 | Siccardi et al. |
| 11,071,573 B2 | 7/2021 | Schneider et al. |
| 11,116,519 B2 | 9/2021 | Sand et al. |
| 11,116,557 B2 | 9/2021 | Zander et al. |
| 11,147,591 B2 | 10/2021 | Jackson |
| 11,147,597 B2 | 10/2021 | Jackson |
| 11,147,688 B2 | 10/2021 | Reckling et al. |
| D935,025 S | 11/2021 | Schifano et al. |
| 11,166,821 B2 | 11/2021 | Sazy |
| 11,172,939 B2 | 11/2021 | Donner et al. |
| 11,224,467 B2 | 1/2022 | Peterson et al. |
| 11,234,830 B2 | 2/2022 | Mesiwala et al. |
| 11,259,854 B2 | 3/2022 | Thornes et al. |
| 11,266,767 B2 | 3/2022 | Roth et al. |
| 11,273,043 B1 | 3/2022 | Abbasi |
| 11,284,798 B2 | 3/2022 | Donner et al. |
| 11,284,887 B2 | 3/2022 | Hartdegen et al. |
| 11,291,485 B2 | 4/2022 | Mauldin et al. |
| 11,298,747 B2 | 4/2022 | Klein et al. |
| D951,455 S | 5/2022 | Ginn |
| 11,318,020 B2 | 5/2022 | Bohl |
| 11,331,123 B2 | 5/2022 | Ballard et al. |
| 11,337,821 B2 | 5/2022 | Mauldin et al. |
| 11,369,419 B2 | 6/2022 | Mesiwala et al. |
| 11,419,653 B2 | 8/2022 | Castro |
| 11,419,654 B2 | 8/2022 | Castro |
| 11,432,829 B2 | 9/2022 | Castro |
| 11,446,069 B2 | 9/2022 | Mauldin et al. |
| 11,452,548 B2 | 9/2022 | Harshman et al. |
| 11,471,286 B2 | 10/2022 | Mauldin et al. |
| 11,478,287 B2 | 10/2022 | Mauldin et al. |
| 11,510,801 B2 | 11/2022 | Archbold |
| D972,137 S | 12/2022 | Schifano et al. |
| 11,517,361 B2 | 12/2022 | Major et al. |
| 11,553,945 B2 | 1/2023 | Castro |
| 11,571,245 B2 | 2/2023 | Stuart et al. |
| 11,580,268 B2 | 2/2023 | Suddaby |
| 11,607,251 B2 | 3/2023 | Albert et al. |
| 11,607,256 B1 | 3/2023 | Folsom et al. |
| 11,737,884 B2 | 8/2023 | Vestgaarden |
| 11,806,197 B2 | 11/2023 | Frey et al. |
| 11,850,156 B2 | 12/2023 | Mauldin et al. |
| 11,883,296 B2 | 1/2024 | Morgenstern Lopez et al. |
| 12,053,208 B2 | 8/2024 | Vitale et al. |
| 12,167,877 B2 | 12/2024 | Harshman et al. |
| 12,245,795 B2 | 3/2025 | Spangler et al. |
| 12,251,320 B2 | 3/2025 | Casey et al. |
| 12,262,918 B2 | 4/2025 | Yacoub et al. |
| 2001/0012942 A1 | 8/2001 | Estes et al. |
| 2001/0046518 A1 | 11/2001 | Sawhney |
| 2001/0047207 A1 | 11/2001 | Michelson |
| 2001/0049529 A1 | 12/2001 | Cachia et al. |
| 2002/0019637 A1 | 2/2002 | Frey et al. |
| 2002/0029043 A1 | 3/2002 | Ahrens et al. |
| 2002/0038123 A1 | 3/2002 | Visotsky et al. |
| 2002/0049497 A1 | 4/2002 | Mason |
| 2002/0077641 A1 | 6/2002 | Michelson |
| 2002/0082598 A1 | 6/2002 | Teitelbaum |
| 2002/0120275 A1 | 8/2002 | Schmieding et al. |
| 2002/0120335 A1 | 8/2002 | Angelucci et al. |
| 2002/0128652 A1 | 9/2002 | Ferree |
| 2002/0143334 A1 | 10/2002 | von Hoffmann et al. |
| 2002/0143335 A1 | 10/2002 | von Hoffmann et al. |
| 2002/0151903 A1 | 10/2002 | Takei et al. |
| 2002/0169507 A1 | 11/2002 | Malone |
| 2002/0183858 A1 | 12/2002 | Contiliano et al. |
| 2002/0198527 A1 | 12/2002 | Mückter |
| 2003/0018336 A1 | 1/2003 | Vandewalle |
| 2003/0032961 A1 | 2/2003 | Pelo et al. |
| 2003/0050642 A1 | 3/2003 | Schmieding et al. |
| 2003/0065332 A1 | 4/2003 | TenHuisen et al. |
| 2003/0074000 A1 | 4/2003 | Roth et al. |
| 2003/0078660 A1 | 4/2003 | Clifford et al. |
| 2003/0083668 A1 | 5/2003 | Rogers et al. |
| 2003/0083688 A1 | 5/2003 | Simonson |
| 2003/0088251 A1 | 5/2003 | Braun et al. |
| 2003/0097131 A1 | 5/2003 | Schon et al. |
| 2003/0139815 A1 | 7/2003 | Grooms et al. |
| 2003/0181979 A1 | 9/2003 | Ferree |
| 2003/0181982 A1 | 9/2003 | Kuslich |
| 2003/0199983 A1 | 10/2003 | Michelson |
| 2003/0229358 A1 | 12/2003 | Errico et al. |
| 2003/0233146 A1 | 12/2003 | Grinberg et al. |
| 2003/0233147 A1 | 12/2003 | Nicholson et al. |
| 2004/0010315 A1 | 1/2004 | Song |
| 2004/0024458 A1 | 2/2004 | Senegas et al. |
| 2004/0034422 A1 | 2/2004 | Errico et al. |
| 2004/0073216 A1 | 4/2004 | Lieberman |
| 2004/0073314 A1 | 4/2004 | White et al. |
| 2004/0082955 A1 | 4/2004 | Zirkle |
| 2004/0087948 A1 | 5/2004 | Suddaby |
| 2004/0097927 A1 | 5/2004 | Yeung et al. |
| 2004/0106925 A1 | 6/2004 | Culbert |
| 2004/0117022 A1 | 6/2004 | Marnay et al. |
| 2004/0127990 A1 | 7/2004 | Bartish, Jr. et al. |
| 2004/0138750 A1 | 7/2004 | Mitchell |
| 2004/0138753 A1 | 7/2004 | Ferree |
| 2004/0147929 A1 | 7/2004 | Biedermann et al. |
| 2004/0158324 A1 | 8/2004 | Lange |
| 2004/0176287 A1 | 9/2004 | Harrison et al. |
| 2004/0176853 A1 | 9/2004 | Sennett et al. |
| 2004/0181282 A1 | 9/2004 | Zucherman et al. |
| 2004/0186572 A1 | 9/2004 | Lange et al. |
| 2004/0210221 A1 | 10/2004 | Kozak et al. |
| 2004/0225360 A1 | 11/2004 | Malone |
| 2004/0230305 A1 | 11/2004 | Gorensek et al. |
| 2004/0260286 A1 | 12/2004 | Ferree |
| 2004/0267369 A1 | 12/2004 | Lyons et al. |
| 2005/0015059 A1 | 1/2005 | Sweeney |
| 2005/0015146 A1 | 1/2005 | Louis et al. |
| 2005/0033435 A1 | 2/2005 | Belliard et al. |
| 2005/0037319 A1 | 2/2005 | Bulard et al. |
| 2005/0049590 A1 | 3/2005 | Alleyne et al. |
| 2005/0055023 A1 | 3/2005 | Sohngen et al. |
| 2005/0070905 A1 | 3/2005 | Donnelly et al. |
| 2005/0070907 A1 | 3/2005 | Abernathie |
| 2005/0071004 A1 | 3/2005 | Re et al. |
| 2005/0075641 A1 | 4/2005 | Singhatat et al. |
| 2005/0080415 A1 | 4/2005 | Keyer et al. |
| 2005/0107878 A1 | 5/2005 | Conchy |
| 2005/0112397 A1 | 5/2005 | Rolfe et al. |
| 2005/0113919 A1 | 5/2005 | Cragg et al. |
| 2005/0124993 A1 | 6/2005 | Chappuis |
| 2005/0131409 A1 | 6/2005 | Chervitz et al. |
| 2005/0137605 A1 | 6/2005 | Assell et al. |
| 2005/0143837 A1 | 6/2005 | Ferree |
| 2005/0149192 A1 | 7/2005 | Zucherman et al. |
| 2005/0159749 A1 | 7/2005 | Levy et al. |
| 2005/0159812 A1 | 7/2005 | Dinger et al. |
| 2005/0165398 A1 | 7/2005 | Reiley |
| 2005/0192572 A1 | 9/2005 | Abdelgany et al. |
| 2005/0216082 A1 | 9/2005 | Wilson et al. |
| 2005/0228384 A1 | 10/2005 | Zucherman et al. |
| 2005/0228388 A1 | 10/2005 | Brodke et al. |
| 2005/0246021 A1 | 11/2005 | Ringeisen et al. |
| 2005/0251146 A1 | 11/2005 | Martz et al. |
| 2005/0273101 A1 | 12/2005 | Schumacher |
| 2005/0277940 A1 | 12/2005 | Neff |
| 2006/0004396 A1 | 1/2006 | Easley et al. |
| 2006/0025771 A1 | 2/2006 | Jackson |
| 2006/0036247 A1 | 2/2006 | Michelson |
| 2006/0036251 A1 | 2/2006 | Reiley |
| 2006/0036252 A1 | 2/2006 | Baynham et al. |
| 2006/0054171 A1 | 3/2006 | Dall |
| 2006/0058793 A1 | 3/2006 | Michelson |

(56) References Cited

U.S. PATENT DOCUMENTS

| | | |
|---|---|---|
| 2006/0058800 A1 | 3/2006 | Ainsworth et al. |
| 2006/0062825 A1 | 3/2006 | Maccecchini |
| 2006/0084986 A1 | 4/2006 | Grinberg et al. |
| 2006/0089644 A1 | 4/2006 | Felix |
| 2006/0089656 A1 | 4/2006 | Allard et al. |
| 2006/0095038 A1 | 5/2006 | Jackson |
| 2006/0111779 A1 | 5/2006 | Petersen |
| 2006/0129247 A1 | 6/2006 | Brown et al. |
| 2006/0142772 A1 | 6/2006 | Ralph et al. |
| 2006/0161163 A1 | 7/2006 | Shino |
| 2006/0178673 A1 | 8/2006 | Curran |
| 2006/0195094 A1 | 8/2006 | McGraw et al. |
| 2006/0217717 A1 | 9/2006 | Whipple |
| 2006/0241600 A1 | 10/2006 | Ensign et al. |
| 2006/0241776 A1 | 10/2006 | Brown et al. |
| 2006/0271054 A1 | 11/2006 | Sucec et al. |
| 2006/0293662 A1 | 12/2006 | Boyer, II et al. |
| 2007/0027544 A1 | 2/2007 | McCord et al. |
| 2007/0038219 A1 | 2/2007 | Matthis et al. |
| 2007/0049933 A1 | 3/2007 | Ahn et al. |
| 2007/0066977 A1 | 3/2007 | Assell et al. |
| 2007/0073295 A1 | 3/2007 | Biederman et al. |
| 2007/0083265 A1 | 4/2007 | Malone |
| 2007/0088362 A1 | 4/2007 | Bonutti et al. |
| 2007/0093841 A1 | 4/2007 | Hoogland |
| 2007/0093898 A1 | 4/2007 | Schwab et al. |
| 2007/0106383 A1 | 5/2007 | Abdou |
| 2007/0149976 A1 | 6/2007 | Hale et al. |
| 2007/0156144 A1 | 7/2007 | Ulrich et al. |
| 2007/0156241 A1 | 7/2007 | Reiley et al. |
| 2007/0156246 A1 | 7/2007 | Meswania et al. |
| 2007/0161985 A1 | 7/2007 | Demakas et al. |
| 2007/0161989 A1 | 7/2007 | Heinz et al. |
| 2007/0173820 A1 | 7/2007 | Trieu |
| 2007/0219634 A1 | 9/2007 | Greenhalgh et al. |
| 2007/0233080 A1 | 10/2007 | Na et al. |
| 2007/0233146 A1 | 10/2007 | Henniges et al. |
| 2007/0233247 A1 | 10/2007 | Schwab |
| 2007/0250166 A1 | 10/2007 | McKay |
| 2007/0270833 A1 | 11/2007 | Bonutti et al. |
| 2007/0270858 A1 | 11/2007 | Trieu et al. |
| 2007/0270879 A1 | 11/2007 | Isaza et al. |
| 2007/0282443 A1 | 12/2007 | Globerman et al. |
| 2008/0021454 A1 | 1/2008 | Chao et al. |
| 2008/0021455 A1 | 1/2008 | Chao et al. |
| 2008/0021456 A1 | 1/2008 | Gupta et al. |
| 2008/0021461 A1 | 1/2008 | Barker et al. |
| 2008/0021480 A1 | 1/2008 | Chin et al. |
| 2008/0065093 A1 | 3/2008 | Assell et al. |
| 2008/0065215 A1 | 3/2008 | Reiley |
| 2008/0071356 A1 | 3/2008 | Greenhalgh et al. |
| 2008/0109083 A1 | 5/2008 | Van Hoeck et al. |
| 2008/0125868 A1 | 5/2008 | Branemark et al. |
| 2008/0132901 A1 | 6/2008 | Recoules-Arche et al. |
| 2008/0140082 A1 | 6/2008 | Erdem et al. |
| 2008/0147079 A1 | 6/2008 | Chin et al. |
| 2008/0154314 A1* | 6/2008 | McDevitt ............... A61F 2/447 623/13.14 |
| 2008/0154374 A1 | 6/2008 | Labrom |
| 2008/0161810 A1 | 7/2008 | Melkent |
| 2008/0161927 A1 | 7/2008 | Savage et al. |
| 2008/0183204 A1 | 7/2008 | Greenhalgh et al. |
| 2008/0234758 A1 | 9/2008 | Fisher et al. |
| 2008/0249579 A1 | 10/2008 | Taylor |
| 2008/0255562 A1 | 10/2008 | Gil et al. |
| 2008/0255618 A1 | 10/2008 | Fisher et al. |
| 2008/0255622 A1 | 10/2008 | Mickiewicz et al. |
| 2008/0255664 A1 | 10/2008 | Hogendijk et al. |
| 2008/0255666 A1 | 10/2008 | Fisher et al. |
| 2008/0255667 A1 | 10/2008 | Horton |
| 2008/0275454 A1 | 11/2008 | Geibel |
| 2008/0294202 A1 | 11/2008 | Peterson et al. |
| 2008/0306554 A1 | 12/2008 | McKinley |
| 2009/0012529 A1 | 1/2009 | Blain et al. |
| 2009/0018660 A1 | 1/2009 | Roush |
| 2009/0024174 A1 | 1/2009 | Stark |
| 2009/0036927 A1 | 2/2009 | Vestgaarden |
| 2009/0037148 A1 | 2/2009 | Lin et al. |
| 2009/0043393 A1 | 2/2009 | Duggal et al. |
| 2009/0082810 A1 | 3/2009 | Bhatnagar et al. |
| 2009/0082869 A1 | 3/2009 | Slemker et al. |
| 2009/0099602 A1 | 4/2009 | Aflatoon |
| 2009/0099610 A1 | 4/2009 | Johnson et al. |
| 2009/0105770 A1 | 4/2009 | Berrevooets et al. |
| 2009/0118771 A1 | 5/2009 | Gonzalez-Hernandez |
| 2009/0131986 A1 | 5/2009 | Lee et al. |
| 2009/0138053 A1 | 5/2009 | Assell et al. |
| 2009/0157119 A1 | 6/2009 | Hale |
| 2009/0163920 A1 | 6/2009 | Hochschuler et al. |
| 2009/0171394 A1 | 7/2009 | Adbou |
| 2009/0187247 A1 | 7/2009 | Metcalf, Jr. et al. |
| 2009/0216238 A1 | 8/2009 | Stark |
| 2009/0270929 A1 | 10/2009 | Suddaby |
| 2009/0287254 A1 | 11/2009 | Nayet et al. |
| 2009/0312798 A1 | 12/2009 | Varela |
| 2009/0319043 A1 | 12/2009 | McDevitt et al. |
| 2009/0324678 A1 | 12/2009 | Thorne et al. |
| 2010/0003638 A1 | 1/2010 | Collins et al. |
| 2010/0022535 A1 | 1/2010 | Lee et al. |
| 2010/0076502 A1 | 3/2010 | Guyer et al. |
| 2010/0081107 A1 | 4/2010 | Bagambisa et al. |
| 2010/0094290 A1 | 4/2010 | Vaidya |
| 2010/0094295 A1 | 4/2010 | Schnieders et al. |
| 2010/0094420 A1 | 4/2010 | Grohowski |
| 2010/0106194 A1 | 4/2010 | Bonutti et al. |
| 2010/0106195 A1 | 4/2010 | Serhan et al. |
| 2010/0114174 A1 | 5/2010 | Jones et al. |
| 2010/0114317 A1 | 5/2010 | Lambrecht et al. |
| 2010/0131011 A1 | 5/2010 | Stark |
| 2010/0137990 A1 | 6/2010 | Apatsidis et al. |
| 2010/0145461 A1 | 6/2010 | Landry et al. |
| 2010/0160977 A1 | 6/2010 | Gephart et al. |
| 2010/0168798 A1 | 7/2010 | Clineff et al. |
| 2010/0191292 A1 | 7/2010 | DeMeo et al. |
| 2010/0228301 A1 | 9/2010 | Greenhalgh et al. |
| 2010/0262242 A1 | 10/2010 | Chavatte et al. |
| 2010/0268228 A1 | 10/2010 | Petersen |
| 2010/0280619 A1 | 11/2010 | Yuan et al. |
| 2010/0280622 A1 | 11/2010 | McKinley |
| 2010/0286778 A1 | 11/2010 | Eisermann et al. |
| 2010/0298889 A1 | 11/2010 | Wilberg et al. |
| 2010/0331851 A1 | 12/2010 | Huene |
| 2010/0331893 A1 | 12/2010 | Geist et al. |
| 2011/0009869 A1 | 1/2011 | Marino et al. |
| 2011/0009966 A1 | 1/2011 | Michelson |
| 2011/0022089 A1 | 1/2011 | Assell et al. |
| 2011/0029019 A1 | 2/2011 | Ainsworth et al. |
| 2011/0040338 A1 | 2/2011 | Jackson |
| 2011/0040362 A1 | 2/2011 | Godara et al. |
| 2011/0046737 A1 | 2/2011 | Teisen |
| 2011/0060373 A1 | 3/2011 | Russell et al. |
| 2011/0060375 A1 | 3/2011 | Bonutti |
| 2011/0066190 A1 | 3/2011 | Schaller et al. |
| 2011/0082551 A1 | 4/2011 | Kraus |
| 2011/0093020 A1 | 4/2011 | Wu |
| 2011/0098747 A1 | 4/2011 | Donner et al. |
| 2011/0098816 A1 | 4/2011 | Jacob et al. |
| 2011/0098817 A1 | 4/2011 | Eckhardt et al. |
| 2011/0106175 A1 | 5/2011 | Rezach |
| 2011/0153018 A1 | 6/2011 | Walters et al. |
| 2011/0160866 A1 | 6/2011 | Laurence et al. |
| 2011/0178561 A1 | 7/2011 | Roh |
| 2011/0184417 A1 | 7/2011 | Kitch et al. |
| 2011/0184518 A1 | 7/2011 | Trieu |
| 2011/0184519 A1 | 7/2011 | Trieu |
| 2011/0184520 A1 | 7/2011 | Trieu |
| 2011/0196372 A1 | 8/2011 | Murase |
| 2011/0213432 A1 | 9/2011 | Geist et al. |
| 2011/0230966 A1 | 9/2011 | Trieu |
| 2011/0238074 A1 | 9/2011 | Ek |
| 2011/0238124 A1 | 9/2011 | Richelsoph |
| 2011/0238181 A1 | 9/2011 | Trieu |
| 2011/0245930 A1 | 10/2011 | Alley et al. |
| 2011/0257755 A1 | 10/2011 | Bellemere et al. |

(56) References Cited

U.S. PATENT DOCUMENTS

| | | |
|---|---|---|
| 2011/0264229 A1 | 10/2011 | Donner |
| 2011/0276098 A1 | 11/2011 | Biedermann et al. |
| 2011/0295272 A1 | 12/2011 | Assell et al. |
| 2011/0295370 A1 | 12/2011 | Suh et al. |
| 2011/0313471 A1 | 12/2011 | McLean et al. |
| 2011/0313532 A1 | 12/2011 | Hunt |
| 2011/0319995 A1 | 12/2011 | Voellmicke et al. |
| 2012/0004730 A1 | 1/2012 | Castro |
| 2012/0035667 A1 | 2/2012 | Van Nortwick et al. |
| 2012/0083887 A1 | 4/2012 | Purcell et al. |
| 2012/0095560 A1 | 4/2012 | Donner |
| 2012/0179256 A1 | 7/2012 | Reiley |
| 2012/0191191 A1 | 7/2012 | Trieu |
| 2012/0215315 A1 | 8/2012 | Hochschuler et al. |
| 2012/0226318 A1 | 9/2012 | Wenger et al. |
| 2012/0253398 A1 | 10/2012 | Metcalf et al. |
| 2012/0271424 A1 | 10/2012 | Crawford |
| 2012/0277866 A1 | 11/2012 | Kalluri et al. |
| 2012/0296428 A1 | 11/2012 | Donner |
| 2012/0323285 A1 | 12/2012 | Assell et al. |
| 2013/0018427 A1 | 1/2013 | Pham et al. |
| 2013/0030456 A1 | 1/2013 | Assell et al. |
| 2013/0030529 A1 | 1/2013 | Hunt |
| 2013/0035727 A1 | 2/2013 | Datta |
| 2013/0053852 A1 | 2/2013 | Greenhalgh et al. |
| 2013/0053854 A1 | 2/2013 | Schoenefeld et al. |
| 2013/0053902 A1 | 2/2013 | Trudeau |
| 2013/0053963 A1 | 2/2013 | Davenport |
| 2013/0072984 A1 | 3/2013 | Robinson |
| 2013/0085535 A1 | 4/2013 | Greenhalgh et al. |
| 2013/0096683 A1 | 4/2013 | Kube |
| 2013/0116793 A1 | 5/2013 | Kloss |
| 2013/0123850 A1 | 5/2013 | Schoenefeld et al. |
| 2013/0123935 A1 | 5/2013 | Hunt et al. |
| 2013/0131678 A1 | 5/2013 | Dahners |
| 2013/0144343 A1 | 6/2013 | Arnett et al. |
| 2013/0158609 A1 | 6/2013 | Mikhail et al. |
| 2013/0172736 A1 | 7/2013 | Abdou |
| 2013/0197590 A1 | 8/2013 | Assell et al. |
| 2013/0203088 A1 | 8/2013 | Baerlecken et al. |
| 2013/0218215 A1 | 8/2013 | Ginn et al. |
| 2013/0218282 A1 | 8/2013 | Hunt |
| 2013/0231746 A1 | 9/2013 | Ginn et al. |
| 2013/0237988 A1 | 9/2013 | Mauldin |
| 2013/0245703 A1 | 9/2013 | Warren et al. |
| 2013/0245763 A1 | 9/2013 | Mauldin |
| 2013/0253595 A1 | 9/2013 | Zucherman et al. |
| 2013/0267836 A1 | 10/2013 | Mauldin et al. |
| 2013/0267961 A1 | 10/2013 | Mauldin et al. |
| 2013/0267989 A1 | 10/2013 | Mauldin et al. |
| 2013/0274890 A1 | 10/2013 | McKay |
| 2013/0325129 A1 | 12/2013 | Huang |
| 2014/0012334 A1 | 1/2014 | Armstrong et al. |
| 2014/0012340 A1 | 1/2014 | Beck et al. |
| 2014/0012384 A1 | 1/2014 | Kana et al. |
| 2014/0031934 A1 | 1/2014 | Trieu |
| 2014/0031935 A1 | 1/2014 | Donner et al. |
| 2014/0031938 A1 | 1/2014 | Lechmann et al. |
| 2014/0031939 A1 | 1/2014 | Wolfe et al. |
| 2014/0046380 A1 | 2/2014 | Asfora |
| 2014/0074175 A1 | 3/2014 | Ehler et al. |
| 2014/0088596 A1 | 3/2014 | Assell et al. |
| 2014/0088707 A1 | 3/2014 | Donner et al. |
| 2014/0121776 A1 | 5/2014 | Hunt |
| 2014/0135927 A1 | 5/2014 | Pavlov et al. |
| 2014/0142700 A1 | 5/2014 | Donner et al. |
| 2014/0172026 A1 | 6/2014 | Biedermann et al. |
| 2014/0172027 A1 | 6/2014 | Biedermann et al. |
| 2014/0200618 A1 | 7/2014 | Donner et al. |
| 2014/0207240 A1 | 7/2014 | Stoffman et al. |
| 2014/0257294 A1 | 9/2014 | Gedet et al. |
| 2014/0257408 A1 | 9/2014 | Trieu et al. |
| 2014/0276846 A1 | 9/2014 | Mauldin et al. |
| 2014/0276851 A1 | 9/2014 | Schneider et al. |
| 2014/0277139 A1 | 9/2014 | Vrionis et al. |
| 2014/0277165 A1 | 9/2014 | Katzman et al. |
| 2014/0277460 A1 | 9/2014 | Schifano et al. |
| 2014/0277462 A1 | 9/2014 | Yerby et al. |
| 2014/0277463 A1 | 9/2014 | Yerby et al. |
| 2014/0288649 A1 | 9/2014 | Hunt |
| 2014/0288650 A1 | 9/2014 | Hunt |
| 2014/0296982 A1 | 10/2014 | Cheng |
| 2014/0330382 A1 | 11/2014 | Mauldin |
| 2014/0364917 A1 | 12/2014 | Sandstrom et al. |
| 2015/0012051 A1 | 1/2015 | Warren et al. |
| 2015/0039037 A1 | 2/2015 | Donner et al. |
| 2015/0080951 A1 | 3/2015 | Yeh |
| 2015/0080972 A1 | 3/2015 | Chin et al. |
| 2015/0094765 A1 | 4/2015 | Donner et al. |
| 2015/0112444 A1 | 4/2015 | Aksu |
| 2015/0147397 A1 | 5/2015 | Altschuler |
| 2015/0150683 A1 | 6/2015 | Donner et al. |
| 2015/0173805 A1 | 6/2015 | Donner et al. |
| 2015/0173904 A1 | 6/2015 | Stark |
| 2015/0182268 A1 | 7/2015 | Donner et al. |
| 2015/0190149 A1 | 7/2015 | Assell et al. |
| 2015/0190187 A1 | 7/2015 | Parent et al. |
| 2015/0209094 A1 | 7/2015 | Anderson |
| 2015/0216566 A1 | 8/2015 | Mikhail et al. |
| 2015/0238203 A1 | 8/2015 | Asfora |
| 2015/0250513 A1* | 9/2015 | De Lavigne Sainte Suzanne ....... A61B 17/864 606/304 |
| 2015/0250611 A1 | 9/2015 | Schifano et al. |
| 2015/0250612 A1 | 9/2015 | Schifano et al. |
| 2015/0257892 A1 | 9/2015 | Lechmann et al. |
| 2015/0313658 A1* | 11/2015 | Kolb .................. A61B 17/8625 606/309 |
| 2015/0313720 A1 | 11/2015 | Lorio |
| 2015/0320450 A1 | 11/2015 | Mootien et al. |
| 2015/0320451 A1 | 11/2015 | Mootien et al. |
| 2015/0320469 A1 | 11/2015 | Biedermann et al. |
| 2015/0342753 A1 | 12/2015 | Donner et al. |
| 2016/0000488 A1 | 1/2016 | Cross, III |
| 2016/0022429 A1 | 1/2016 | Greenhalgh et al. |
| 2016/0095711 A1 | 4/2016 | Castro |
| 2016/0095721 A1 | 4/2016 | Schell et al. |
| 2016/0100870 A1 | 4/2016 | Lavigne et al. |
| 2016/0106477 A1 | 4/2016 | Hynes et al. |
| 2016/0106479 A1 | 4/2016 | Hynes et al. |
| 2016/0120661 A1 | 5/2016 | Schell et al. |
| 2016/0143671 A1 | 5/2016 | Jimenez |
| 2016/0157908 A1 | 6/2016 | Cawley et al. |
| 2016/0166291 A1 | 6/2016 | Goel et al. |
| 2016/0166301 A1* | 6/2016 | Papangelou ....... A61B 17/7035 606/232 |
| 2016/0175113 A1 | 6/2016 | Lins |
| 2016/0184103 A1 | 6/2016 | Fonte et al. |
| 2016/0213487 A1 | 7/2016 | Wilson et al. |
| 2016/0242820 A1 | 8/2016 | Whipple et al. |
| 2016/0242912 A1 | 8/2016 | Lindsey et al. |
| 2016/0249940 A1 | 9/2016 | Stark |
| 2016/0287171 A1 | 10/2016 | Sand et al. |
| 2016/0287301 A1 | 10/2016 | Mehl et al. |
| 2016/0310188 A1 | 10/2016 | Marino et al. |
| 2016/0310197 A1 | 10/2016 | Black et al. |
| 2016/0324643 A1 | 11/2016 | Donner et al. |
| 2016/0324656 A1 | 11/2016 | Morris et al. |
| 2016/0374727 A1 | 12/2016 | Greenhalgh et al. |
| 2017/0014235 A1 | 1/2017 | Jones et al. |
| 2017/0020573 A1 | 1/2017 | Cain et al. |
| 2017/0020585 A1 | 1/2017 | Harshman et al. |
| 2017/0086885 A1 | 3/2017 | Duncan et al. |
| 2017/0128083 A1 | 5/2017 | Germain |
| 2017/0128214 A1 | 5/2017 | Mayer |
| 2017/0135733 A1 | 5/2017 | Donner et al. |
| 2017/0135737 A1 | 5/2017 | Krause |
| 2017/0143513 A1 | 5/2017 | Sandstrom et al. |
| 2017/0156879 A1 | 6/2017 | Janowski |
| 2017/0156880 A1 | 6/2017 | Halverson et al. |
| 2017/0202511 A1 | 7/2017 | Chang et al. |
| 2017/0209155 A1 | 7/2017 | Petersen |
| 2017/0216036 A1 | 8/2017 | Cordaro |
| 2017/0224393 A1 | 8/2017 | Lavigne et al. |

(56) References Cited

U.S. PATENT DOCUMENTS

| | | |
|---|---|---|
| 2017/0246000 A1 | 8/2017 | Pavlov et al. |
| 2017/0258498 A1 | 9/2017 | Redmond et al. |
| 2017/0258506 A1 | 9/2017 | Redmond et al. |
| 2017/0258606 A1 | 9/2017 | Afzal |
| 2017/0266007 A1 | 9/2017 | Gelaude et al. |
| 2017/0296344 A1 | 10/2017 | Souza et al. |
| 2017/0303938 A1 | 10/2017 | Rindal et al. |
| 2017/0333205 A1 | 11/2017 | Joly et al. |
| 2017/0348034 A1 | 12/2017 | LaPierre et al. |
| 2017/0354442 A1 | 12/2017 | Kim et al. |
| 2017/0360570 A1 | 12/2017 | Berndt et al. |
| 2018/0008256 A1 | 1/2018 | Fallin et al. |
| 2018/0036041 A1 | 2/2018 | Pham et al. |
| 2018/0042652 A1 | 2/2018 | Mari et al. |
| 2018/0042735 A1 | 2/2018 | Schell et al. |
| 2018/0092677 A1 | 4/2018 | Peterson et al. |
| 2018/0104063 A1 | 4/2018 | Asaad |
| 2018/0104068 A1 | 4/2018 | Sack |
| 2018/0110624 A1 | 4/2018 | Arnone |
| 2018/0110626 A1 | 4/2018 | McShane, III et al. |
| 2018/0200063 A1 | 7/2018 | Kahmer et al. |
| 2018/0214192 A1 | 8/2018 | Roby et al. |
| 2018/0228613 A1 | 8/2018 | Jones et al. |
| 2018/0228617 A1 | 8/2018 | Srour et al. |
| 2018/0228621 A1 | 8/2018 | Reiley et al. |
| 2018/0235643 A1 | 8/2018 | Lins et al. |
| 2018/0243097 A1 | 8/2018 | Jones et al. |
| 2018/0256232 A1 | 9/2018 | Russell |
| 2018/0256351 A1 | 9/2018 | Bishop et al. |
| 2018/0256352 A1 | 9/2018 | Nyahay et al. |
| 2018/0256361 A1 | 9/2018 | Bishop et al. |
| 2018/0280139 A1 | 10/2018 | Jones et al. |
| 2018/0280140 A1 | 10/2018 | Jones et al. |
| 2018/0289504 A1 | 10/2018 | Arthurs et al. |
| 2018/0296227 A1 | 10/2018 | Meek et al. |
| 2018/0296347 A1 | 10/2018 | Hamzey et al. |
| 2018/0296363 A1 | 10/2018 | Berry |
| 2018/0303520 A1 | 10/2018 | Rajpal |
| 2018/0303623 A1 | 10/2018 | Shoshtaev |
| 2018/0303624 A1 | 10/2018 | Shoshtaev |
| 2018/0317971 A1 | 11/2018 | Prevost |
| 2018/0360512 A1 | 12/2018 | Mari |
| 2018/0368894 A1 | 12/2018 | Wieland et al. |
| 2019/0000636 A1 | 1/2019 | Kim et al. |
| 2019/0008562 A1 | 1/2019 | Melton et al. |
| 2019/0046684 A1 | 2/2019 | Roth |
| 2019/0076258 A1 | 3/2019 | Black et al. |
| 2019/0076266 A1 | 3/2019 | Trudeau et al. |
| 2019/0083270 A1 | 3/2019 | Milz et al. |
| 2019/0091027 A1 | 3/2019 | Asaad et al. |
| 2019/0117827 A1 | 4/2019 | Roth |
| 2019/0125371 A1 | 5/2019 | Asfora et al. |
| 2019/0125408 A1 | 5/2019 | Asfora et al. |
| 2019/0133613 A1 | 5/2019 | Reiley et al. |
| 2019/0133769 A1 | 5/2019 | Tetsworth et al. |
| 2019/0133783 A1 | 5/2019 | Unger et al. |
| 2019/0142606 A1 | 5/2019 | Freudenberger |
| 2019/0150910 A1 | 5/2019 | Jones et al. |
| 2019/0151113 A1 | 5/2019 | Sack |
| 2019/0151114 A1 | 5/2019 | Sack |
| 2019/0167326 A1 | 6/2019 | Greenhalgh et al. |
| 2019/0183653 A1 | 6/2019 | Gregersen et al. |
| 2019/0231554 A1 | 8/2019 | Bishop et al. |
| 2019/0239935 A1 | 8/2019 | Willis et al. |
| 2019/0247094 A1 | 8/2019 | Yacoub et al. |
| 2019/0254840 A1 | 8/2019 | Gray et al. |
| 2019/0262048 A1 | 8/2019 | Sutika |
| 2019/0262049 A1 | 8/2019 | Tempco et al. |
| 2019/0290441 A1 | 9/2019 | Tong et al. |
| 2019/0298528 A1 | 10/2019 | Lindsey et al. |
| 2019/0298542 A1 | 10/2019 | Kloss |
| 2019/0328546 A1 | 10/2019 | Palagi et al. |
| 2019/0343564 A1 | 11/2019 | Tempco et al. |
| 2019/0343565 A1 | 11/2019 | Tempco et al. |
| 2019/0343566 A1 | 11/2019 | Tempco et al. |
| 2019/0343567 A1 | 11/2019 | Tempco et al. |
| 2019/0343640 A1 | 11/2019 | Donner et al. |
| 2019/0343644 A1 | 11/2019 | Ryan et al. |
| 2019/0343645 A1 | 11/2019 | Miccio et al. |
| 2019/0343652 A1 | 11/2019 | Petersheim et al. |
| 2019/0343653 A1 | 11/2019 | McKay |
| 2019/0388131 A1 | 12/2019 | Mehl et al. |
| 2019/0388228 A1 | 12/2019 | Donner et al. |
| 2019/0388242 A1 | 12/2019 | Harris et al. |
| 2020/0000595 A1 | 1/2020 | Jones et al. |
| 2020/0008817 A1 | 1/2020 | Reiley et al. |
| 2020/0022817 A1 | 1/2020 | Crossgrove et al. |
| 2020/0038069 A1 | 2/2020 | Jones et al. |
| 2020/0046512 A1 | 2/2020 | Newman et al. |
| 2020/0069431 A1 | 3/2020 | Boehm et al. |
| 2020/0100822 A1 | 4/2020 | Lipow |
| 2020/0129214 A1 | 4/2020 | Pepper et al. |
| 2020/0138485 A1 | 5/2020 | Kuwamura et al. |
| 2020/0138492 A1 | 5/2020 | Kavanagh |
| 2020/0146721 A1 | 5/2020 | Sadiq |
| 2020/0149137 A1 | 5/2020 | Roth |
| 2020/0170679 A1 | 6/2020 | Sciubba et al. |
| 2020/0206390 A1 | 7/2020 | Roth |
| 2020/0222088 A1 | 7/2020 | Kraus |
| 2020/0222195 A1 | 7/2020 | Assell et al. |
| 2020/0246158 A1 | 8/2020 | Bergey |
| 2020/0254140 A1 | 8/2020 | Roth |
| 2020/0268449 A1 | 8/2020 | Solitro et al. |
| 2020/0268518 A1 | 8/2020 | Suh et al. |
| 2020/0281729 A1 | 9/2020 | Schifano et al. |
| 2020/0297496 A1 | 9/2020 | Mullin |
| 2020/0305896 A1 | 10/2020 | Castro |
| 2020/0315647 A1 | 10/2020 | Fojtik et al. |
| 2020/0315666 A1 | 10/2020 | Nichols et al. |
| 2020/0315669 A1 | 10/2020 | Dejardin |
| 2020/0345507 A1 | 11/2020 | Reiley |
| 2020/0345508 A1 | 11/2020 | Reiley |
| 2020/0345509 A1 | 11/2020 | Reiley |
| 2020/0345510 A1 | 11/2020 | Reiley |
| 2020/0375750 A1 | 12/2020 | Abbasi et al. |
| 2020/0397491 A1 | 12/2020 | Frey et al. |
| 2021/0022882 A1 | 1/2021 | Dang et al. |
| 2021/0107093 A1 | 4/2021 | Tempco |
| 2021/0153911 A1 | 5/2021 | Stuart et al. |
| 2021/0169660 A1 | 6/2021 | Reckling et al. |
| 2021/0196332 A1 | 7/2021 | Patel |
| 2021/0212734 A1 | 7/2021 | Mesiwala et al. |
| 2021/0228360 A1 | 7/2021 | Hunt et al. |
| 2021/0236146 A1 | 8/2021 | Donner et al. |
| 2021/0338454 A1 | 11/2021 | Afzal |
| 2021/0346038 A1 | 11/2021 | Fiechter et al. |
| 2021/0353337 A1 | 11/2021 | Kaufmann et al. |
| 2021/0353338 A1 | 11/2021 | Meek et al. |
| 2021/0393298 A1 | 12/2021 | Castro |
| 2021/0393408 A1 | 12/2021 | Ginn |
| 2021/0393409 A1 | 12/2021 | Ginn |
| 2022/0031365 A1 | 2/2022 | Suh et al. |
| 2022/0031474 A1 | 2/2022 | Reckling et al. |
| 2022/0096098 A1 | 3/2022 | Sand et al. |
| 2022/0117640 A1 | 4/2022 | Schneider et al. |
| 2022/0273447 A1 | 9/2022 | Ginn |
| 2022/0273448 A1 | 9/2022 | Ginn et al. |
| 2022/0280303 A1 | 9/2022 | Mauldin et al. |
| 2022/0296377 A1 | 9/2022 | Ginn et al. |
| 2022/0296378 A1 | 9/2022 | Ginn |
| 2022/0304813 A1 | 9/2022 | Ginn et al. |
| 2022/0304814 A1 | 9/2022 | Ginn |
| 2022/0354665 A1 | 11/2022 | Mesiwala et al. |
| 2022/0409381 A1 | 12/2022 | Ginn |
| 2023/0000526 A1 | 1/2023 | Follini et al. |
| 2023/0000630 A1 | 1/2023 | Ginn et al. |
| 2023/0000631 A1 | 1/2023 | Ginn et al. |
| 2023/0000639 A1 | 1/2023 | Stuart et al. |
| 2023/0076180 A1 | 3/2023 | Schifano et al. |
| 2023/0190442 A1 | 6/2023 | Castro |
| 2023/0263553 A1 | 8/2023 | Compton et al. |
| 2023/0263554 A1 | 8/2023 | Stuart et al. |
| 2023/0270559 A1 | 8/2023 | Mesiwala et al. |
| 2023/0285054 A1 | 9/2023 | Mehl et al. |

(56) References Cited

U.S. PATENT DOCUMENTS

| | | |
|---|---|---|
| 2023/0293206 A1 | 9/2023 | Mundis, Jr. et al. |
| 2023/0321317 A1 | 10/2023 | Suh |
| 2023/0329765 A1 | 10/2023 | Lavigne et al. |
| 2023/0390078 A1 | 12/2023 | Bergey et al. |
| 2023/0404762 A1 | 12/2023 | Ginn et al. |
| 2024/0050131 A1 | 2/2024 | Bannigan et al. |
| 2024/0252717 A1 | 8/2024 | Suh et al. |
| 2024/0261107 A1 | 8/2024 | Ginn et al. |
| 2024/0285410 A1 | 8/2024 | Ginn et al. |
| 2024/0366401 A1 | 11/2024 | Bergey |
| 2024/0374399 A1 | 11/2024 | Stuart et al. |
| 2024/0390151 A1 | 11/2024 | Ginn et al. |
| 2024/0398453 A1 | 12/2024 | Mauldin et al. |
| 2024/0415547 A1 | 12/2024 | Wentz et al. |
| 2025/0009396 A1 | 1/2025 | Vestgaarden |
| 2025/0025309 A1 | 1/2025 | Casey |
| 2025/0099259 A1 | 3/2025 | Cordaro |

FOREIGN PATENT DOCUMENTS

| | | | |
|---|---|---|---|
| CN | 1909848 A | 2/2007 | |
| CN | 101795632 A | 8/2010 | |
| CN | 102361601 A | 2/2012 | |
| CN | 102429716 A * | 5/2012 | ......... A61B 17/7032 |
| CN | 104968283 A | 10/2015 | |
| CN | 109124748 A | 6/2017 | |
| DE | 102011001264 A1 | 9/2012 | |
| DE | 102012106336 A1 | 1/2014 | |
| EP | 1287796 A1 | 3/2003 | |
| EP | 2070481 B1 | 2/2012 | |
| EP | 2796104 A1 | 10/2014 | |
| EP | 2590576 B1 | 10/2015 | |
| EP | 2749238 B1 | 3/2017 | |
| EP | 2887899 B1 | 8/2017 | |
| EP | 2341852 B1 | 8/2018 | |
| EP | 2496162 B1 | 10/2018 | |
| EP | 3484387 A1 | 5/2019 | |
| EP | 3501457 A1 | 6/2019 | |
| EP | 356044/8 A1 | 10/2019 | |
| EP | 3593745 A2 | 1/2020 | |
| EP | 3616634 A1 | 3/2020 | |
| EP | 3661441 A1 | 6/2020 | |
| EP | 2408389 B1 | 4/2021 | |
| JP | 59200642 A | 11/1984 | |
| JP | 05-176942 A | 7/1993 | |
| JP | 05184615 A | 7/1993 | |
| JP | 09149906 A | 10/1997 | |
| JP | 10-85231 A | 4/1998 | |
| JP | 11318931 A | 11/1999 | |
| JP | 2002509753 A | 4/2002 | |
| JP | 2003511198 A | 3/2003 | |
| JP | 2003533329 A | 11/2003 | |
| JP | 2003534046 A | 11/2003 | |
| JP | 2004121841 | 4/2004 | |
| JP | 2004512895 | 4/2004 | |
| JP | 2004516866 | 6/2004 | |
| JP | 2006506181 | 2/2006 | |
| JP | 2007535973 A | 12/2007 | |
| JP | 2008540036 A | 11/2008 | |
| JP | 2009000501 A | 1/2009 | |
| JP | 2009521990 A | 6/2009 | |
| JP | 2009533159 A | 9/2009 | |
| JP | 2010137016 A | 6/2010 | |
| JP | 2011041802 A | 3/2011 | |
| JP | 2011512939 A | 4/2011 | |
| JP | 2012030105 A | 2/2012 | |
| JP | 2014000402 A | 1/2014 | |
| JP | 2014147820 A | 8/2014 | |
| JP | 2015510506 A | 4/2015 | |
| JP | 2015171520 A | 10/2015 | |
| JP | 2015531282 A | 11/2015 | |
| JP | 2016515857 A | 6/2016 | |
| JP | 2017528251 A | 9/2017 | |
| JP | 2017533759 A | 11/2017 | |
| JP | 2019506993 A | 3/2019 | |
| WO | WO97/31517 A2 | 8/1997 | |
| WO | WO01/17445 A1 | 3/2001 | |
| WO | WO02/38054 | 5/2002 | |
| WO | WO03/007839 A2 | 1/2003 | |
| WO | WO04/02344 | 1/2004 | |
| WO | WO2004/043277 A1 | 5/2004 | |
| WO | WO2005/009729 A2 | 2/2005 | |
| WO | WO2006/003316 | 1/2006 | |
| WO | WO2006/023793 A2 | 3/2006 | |
| WO | WO2006/074321 A2 | 7/2006 | |
| WO | WO2006/116850 A1 | 11/2006 | |
| WO | WO2008/153723 A1 | 12/2008 | |
| WO | WO2009/025884 A2 | 2/2009 | |
| WO | WO2009/029074 A1 | 3/2009 | |
| WO | WO2010/105196 A1 | 9/2010 | |
| WO | WO2011/010463 A1 | 1/2011 | |
| WO | WO2011/110865 A2 | 9/2011 | |
| WO | WO2011/124874 A1 | 10/2011 | |
| WO | WO2011/149557 A1 | 12/2011 | |
| WO | WO2012/015976 A1 | 2/2012 | |
| WO | WO2012/048008 A1 | 4/2012 | |
| WO | WO2013/000071 A1 | 1/2013 | |
| WO | WO2013/052807 A2 | 4/2013 | |
| WO | WO2013/119907 A1 | 8/2013 | |
| WO | WO2013/134678 A1 | 9/2013 | |
| WO | WO2014/145902 A1 | 9/2014 | |
| WO | WO2017/147140 A1 | 8/2017 | |
| WO | WO2017/147537 A1 | 8/2017 | |
| WO | WO-2017201371 A1 * | 11/2017 | ............... A61F 2/28 |
| WO | WO2019/152737 A1 | 8/2019 | |
| WO | WO2020/168269 A1 | 8/2020 | |

OTHER PUBLICATIONS

Al-Khayer et al.; Percutaneous sacroiliac joint arthrodesis, a novel technique; J Spinal Disord Tech; vol. 21; No. 5; pp. 359-363; Jul. 2008.

Eisner; New SI Joint Fusion System Cleared; Orthopedics This Week; Jun. 28, 2018; retreived from the internet <https://ryortho.com/breaking/new-si-joint-fusion-system-cleared/> on Sep. 8, 2022; 5 pages.

Khurana et al.; Percutaneous fusion of the sacroiliac joint with hollow modular anchorage screws, clinical and radiological outcome; J Bone Joint Surg; vol. 91-B; No. 5; pp. 627-631; May 2009.

Lu et al.; Mechanical properties of porous materials; Journal of Porous Materials; 6(4); pp. 359-368; Nov. 1, 1999.

Peretz et al.; The internal bony architecture of the sacrum; Spine; 23(9); pp. 971-974; May 1, 1998.

Richards et al.; Bone density and cortical thickness in normal, osteopenic, and osteoporotic sacra; Journal of Osteoporosis; 2010(ID 504078); 5 pgs; Jun. 9, 2010.

Wise et al.; Minimally invasive sacroiliac arthrodesis, outcomes of a new technique; J Spinal Disord Tech; vol. 21; No. 8; pp. 579-584; Dec. 2008.

Third Party Observation; PCT/US2021/062337; Aug. 29, 2022; 6 pages.

Mesiwala et al.; U.S. Appl. No. 17/649,265 entitled "Implants for spinal fixation and or fusion," filed Jan. 28, 2022.

Mauldin et al.; U.S. Appl. No. 17/805,165 entitled "Systems, device, and methods for joint fusion," filed Jun. 2, 2022.

Mauldin et al.; U.S. Appl. No. 17/822,360 entitled "Fenestrated implant," filed Aug. 25, 2022.

Reiley et al.; U.S. Appl. No. 18/317,832 entitled "Implants for bone fixation or fusion," filed May 15, 2023.

Stuart et al.; U.S. Appl. No. 18/356,880 entitled "Sacro-iliac join stabilizing implants and methods of implantation," filed Jul. 21, 2023.

Mauldin et al.; U.S. Appl. No. 18/509,864 entitled "Systems, device, and methods for joint fusion," filed Nov. 15, 2023.

Sand et al.; U.S. Appl. No. 18/527,030 entitled "Systems and methods for decorticating the sacroiliac joint," filed Dec. 1, 2023.

Mesiwala et al.; U.S. Appl. No. 18/632,102 entitled "Implants for spinal fixation or fusion," filed Apr. 10, 2024.

Schneider et al.; U.S. Appl. No. 18/927,238 entitled "Matrix implant," filed Oct. 25, 2024.

(56) References Cited

OTHER PUBLICATIONS

Mesiwala et al.; U.S. Appl. No. 18/716,090 entitled "Fusion cages and methods for sacro-iliac joint stabilization," filed Jun. 3, 2024.
Stuart et al.; U.S. Appl. No. 18/805,412 entitled "Pelvic stabilization implants, methods of use and manufacture," filed Aug. 14, 2024.
Reckling et al.; U.S. Appl. No. 18/809,229 entitled "Sacro-iliac joint stabilizing implants and methods of implantation," filed Aug. 19, 2024.
Mesiwala et al.; U.S. Appl. No. 18/810,211 entitled "Implants for spinal fixation and or fusion," filed Aug. 20, 2024.
Polly et al.; U.S. Appl. No. 19/024,752 entitled "Spine stabilization," filed Jan. 16, 2025.
Sand et al.; U.S. Appl. No. 18/951,349 entitled "Systems, devices, and methods for preparing bone to receive an implant," filed Nov. 18, 2024.
Sand et al.; U.S. Appl. No. 18/951,396 entitled "Sacroiliac joint stabilization, including implants, systems and methods of delivering implants," filed Nov. 18, 2024.
Anderson Jr et al.; U.S. Appl. No. 18/870,896 entitled "Bi-lateral pelvic stabilization," filed Dec. 2, 2024.
Stuart et al.; U.S. Appl. No. 18/977,789 entitled "Bone stabilizing implants and methods of placement across si joints," filed Dec. 11, 2024.

\* cited by examiner (Anterior)

(Posterior)

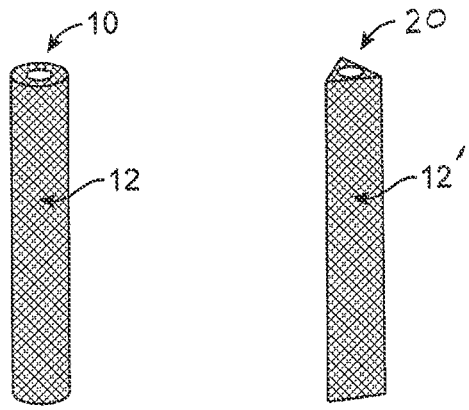
FIG. 3
(PRIOR ART)
FIG. 4
(PRIOR ART)
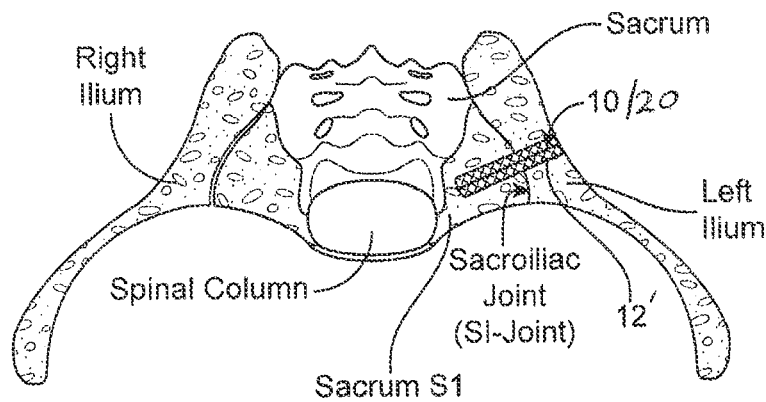
FIG. 5
(PRIOR ART)
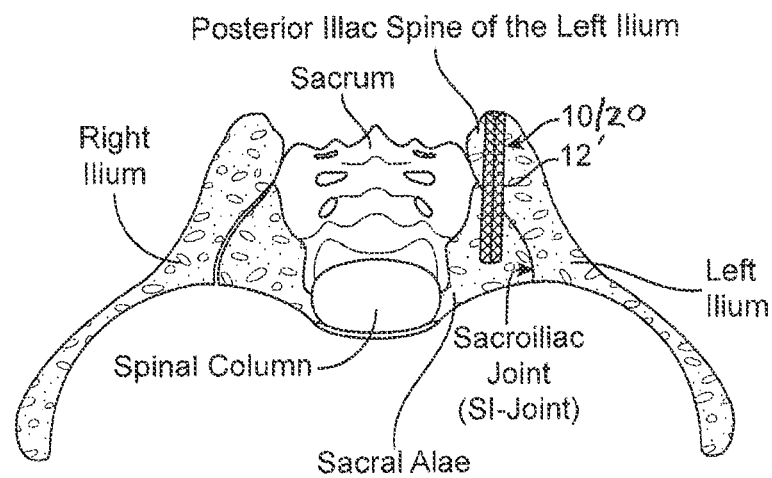
FIG. 6
(PRIOR ART)

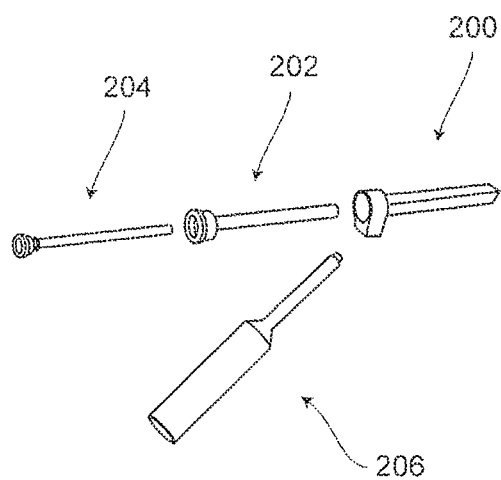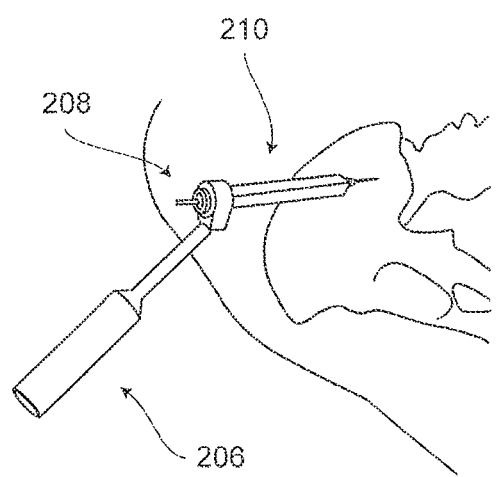
FIG. 7E
(PRIOR ART)
FIG. 7F
(PRIOR ART)

THREADED IMPLANTS AND METHODS OF USE ACROSS BONE SEGMENTS

CROSS REFERENCE TO RELATED APPLICATIONS

This application is a continuation of U.S. application Ser. No. 16/368,686, filed Mar. 28, 2019, which claims the benefit of U.S. Provisional Application No. 62/649,466 filed Mar. 28, 2018, each of which are herein incorporated by reference in its entirety.

INCORPORATION BY REFERENCE

All publications and patent applications mentioned in this specification are herein incorporated by reference for all intents and purposes to the same extent as if each individual publication or patent application was specifically and individually indicated to be incorporated by reference.

FIELD

Embodiments of the disclosure relate generally to fixation or fusion of a bone joint or fracture, and more specifically, to threaded devices and methods of implanting the devices across bone segments.

BACKGROUND

Sacroiliac joint (SI-Joint) fusion is a surgical procedure that is performed to alleviate pain coming from the SI-Joint in patients who have failed to receive adequate pain relief with non-surgical treatments of the SI-Joint. Some conditions of the SI-Joint that may be treated with SI-Joint fusion (arthrodesis) are: degenerative sacroiliitis, inflammatory sacroiliitis, iatrogenic instability of the sacroiliac joint, osteitis condensans ilii, or traumatic fracture dislocation of the pelvis. Historically, screws and screws with plates were used as the standard instrumentation for sacro-iliac fusion. An SI-Joint fusion consisted of an open surgical approach to the SI-Joint from an anterior, a posterior, or a lateral direction. The surgeon would then debride (remove) the cartilage from the articular portion of the joint and the interosseous ligament from the fibrous portion of the joint. These open approaches require a large incision and deep soft tissue dissection to approach the damaged, subluxed, dislocated, fractured, or degenerative SI-Joint.

With more recent advancements in SI-Joint surgery, a typical technique for placing implants involves placement of one or multiple implants from a lateral to medial direction across the SI-Joint. These implants are placed with a starting point on the lateral aspect of the ilium. The implants are then directed across the ilium, across the sacroiliac joint and into the sacrum.

Various styles of implants are available today for fusing the SI-Joint and other joints in the above minimally invasive surgeries. However, it would be desirable to provide improved implants and methods to promote even faster and stronger fusion of bone joints.

BRIEF DESCRIPTION OF THE DRAWINGS

A better understanding of the features and advantages of the present disclosure will be obtained by reference to the following detailed description that sets forth illustrative embodiments, in which the principles of the disclosure are utilized, and the accompanying drawings of which:

FIGS. 3 and 4 are embodiments of various implants that can be used for the fusion or fixation of a joint or two bone segments.

FIG. 5 illustrates an axial section view of the SI-Joint with an implant for the fixation of the SI-Joint using a lateral approach that goes laterally through the ilium, the SI-Joint, and into the sacrum 51.

FIG. 6 illustrates an axial section view of the SI-Joint with an implant for the fixation of the SI-Joint using a posterolateral approach entering from the posterior iliac spine of the ilium, angling through the SI-Joint, and terminating in the sacral alae.

FIGS. 7E and 7F illustrate the assembly of a soft tissue protector system for placement over a guide wire.

SUMMARY OF THE DISCLOSURE

Figure 1:
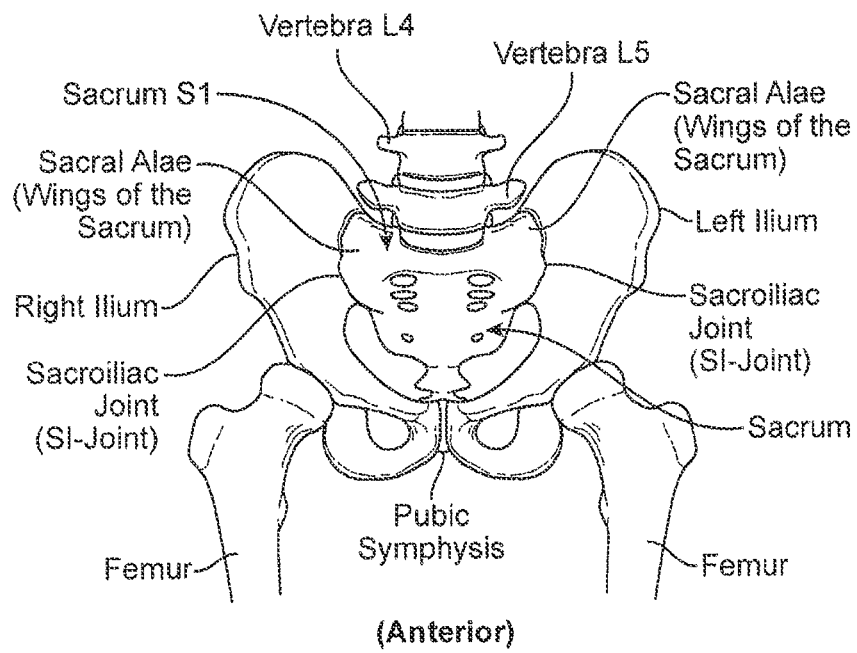
FIGS. 1 and 2 are, respectively, anterior and posterior anatomic views of the human hip girdle comprising the sacrum and the hip bones (the right ilium, and the left ilium), the sacrum being connected with both hip bones at the sacroiliac joint (in shorthand, the SI-Joint).

According to aspects of the present disclosure, a threaded implant can be provided with an elongated main body having external threads configured to thread into bone, and an internal support structure located within the external threads. The internal support structure has a helical arrangement that extends in an opposite direction to the external threads. The threaded implant may further include a drive socket located on a proximal end of the main body and configured to receive a tip of a drive tool for rotationally driving the implant into bone. In some embodiments, a through bore is provided along a central longitudinal axis of the main body from a proximal end to a distal end. The external threads may have a single start and the internal support structure may have four starts. In some embodiments, the internal support structure has a pitch that is eight time the pitch of the external threads. The implant may further include fenestrations or interstices between the external threads and the internal support structure. The fenestrations or interstices may be filled with a porous infill which provides scaffolding with increased surface area for new bone growth. In some embodiments, the porous infill is at least 20% more porous than the external threads and the internal support structure.

According to other aspects of the present disclosure, a threaded implant can be provided with an elongated main body, a first set of threads, a second set of threads and a sleeve. The main body has a proximal end, a mid-section and a distal end. The first set of threads is provided along the proximal end of the main body and the second set of threads is provided along the distal end. The sleeve is located on the mid-section of the main body such that it may rotate with respect to the main body while being constrained from axial movement. In some embodiments, the sleeve has a transverse cross-section that is rectilinear, has at least one apex and/or is triangular in shape. The second set of threads may have a pitch that is greater than a pitch of the first set of threads.

According to other aspects of the present disclosure, a threaded implant can be provided with an elongated main body, a head portion and a threaded portion. The elongated main body has a proximal end, a mid-section and a distal end. The head portion is located on the proximal end of the main body and configured to abut against an outer surface of a bone segment. The threaded portion is located on the distal end of the main body and has a transverse cross-section that is triangular in shape. In some embodiments, the implant is provided a drive socket located on the proximal end of the main body and configured to receive a tip of a drive tool for rotationally driving the implant into bone.

According to other aspects of the present disclosure, a threaded implant can be provided with an elongated main body, a proximal screw, a proximal screw cap and at least one rotation stop. The elongated main body has a proximal end, a mid-section and a distal end.

DETAILED DESCRIPTION

A joint of a patient can be decorticated or selectively decorticated in order to promote bone regeneration and fusion at the implant site. Many types of hardware are available both for the fixation of bones that are fractured and for the fixation of bones that are to be fused (arthrodesed). While the following examples focus on the SI-Joint, the methods, instrumentation and implants disclosed herein may be used for decortication of other body joints as well.

Figure 2:
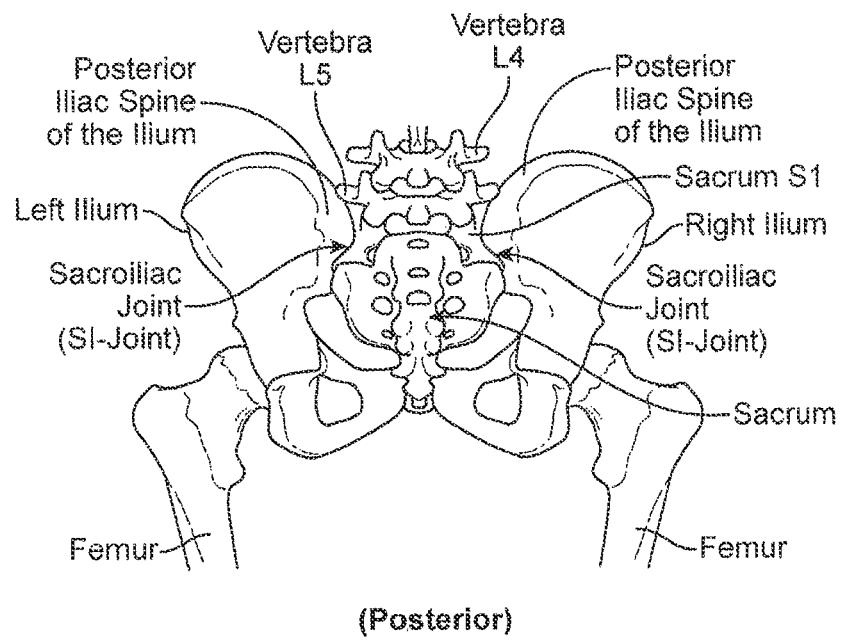

Referring to FIGS. 1 and 2, the human hip girdle is made up of three large bones joined by three relatively immobile joints. One of the bones is called the sacrum and it lies at the bottom of the lumbar spine, where it connects with the L5 vertebra. The other two bones are commonly called "hip bones" and are technically referred to as the right ilium and the left ilium. The sacrum connects with both hip bones at the sacroiliac joint (in shorthand, the SI-Joint).

The SI-Joint functions in the transmission of forces from the spine to the lower extremities, and vice-versa. The SI-Joint has been described as a pain generator for up to 22% of lower back pain patients.

To relieve pain generated from the SI-Joint, sacroiliac joint fusion is typically indicated as surgical treatment, e.g., for degenerative sacroiliitis, inflammatory sacroiliitis, iatrogenic instability of the sacroiliac joint, osteitis condensans ilii, or traumatic fracture dislocation of the pelvis. In some currently performed procedures, screws or screws with plates are used for sacro-iliac fusion. At the time of the procedure, articular cartilage may be removed from the "synovial joint" portion of the SI-Joint. This can require a large incision to approach the damaged, subluxed, dislocated, fractured, or degenerated joint. The large incision and removal of tissue can cause significant trauma to the patient, resulting in pain and increasing the time to heal after surgery.

In addition, screw type implants tend to be susceptible to rotation and loosening, especially in joints that are subjected to torsional forces, such as the SI-Joint. Excessive movement of the implant after implantation may result in the failure of the implant to incorporate and fuse with the bone, which may result in the need to remove and replace the failed implant.

FIG. 3 and FIG. 4 illustrate straight implants 10 and 20, respectively, with a solid elongate body 12 or 12' that can be used for the fixation or fusion of two bone segments. The implant 10 shown in FIG. 3 is cylindrical and can optionally have screw threads along the exterior of the implant body. As mentioned above, cylindrical screw type implants can suffer from excessive rotation. One solution to this problem is the implant 20 in FIG. 4, which has a non-cylindrical cross-sectional area. For example, as shown, the implant 20 can have a triangular cross-sectional area, although other rectilinear cross-sectional profiles may be used as well, including rectangular, hexagonal and the like. Non-cylindrical implants need not have a strict rectilinear cross-sectional profile in order to resist rotation. A cross-sectional area that is non-circular will generally suffice. For example, a tear drop shaped cross-sectional area, or a cross-sectional area with at least one apex, can resist rotation. Other non-circular cross-sectional geometries that may not have a rectilinear component can also work, such as oval cross-sections.

FIG. 5 illustrates insertion of the implant 10 or 20 of FIG. 3 or FIG. 4 across the SI-Joint using a lateral approach that goes laterally through the ilium, across the SI-Joint, and into the sacrum. FIG. 6 illustrates insertion of the same implant across the SI-Joint using a postero-lateral approach entering from the posterior iliac spine of the ilium, angling through the SI-Joint, and terminating in the sacral alae. The implants and instrumentation described herein typically can be inserted across the SI-Joint according to one of these two approaches, or with a similar approach.

Referring to FIGS. 7-10, an exemplary method for fixation of the SI-Joint will be described. Elongated, stem-like implant structures 10 or 20 like those shown in FIGS. 3 and 4 make possible the fixation of the SI-Joint in a minimally invasive manner. These implant structures can be effectively implanted through the use a lateral surgical approach (as shown in FIG. 5). The procedure may be aided by conventional lateral, inlet, and outlet visualization techniques, e.g., using X-ray image intensifiers such as a C-arms or fluoroscopes to produce a live image feed, which is displayed on a TV screen.

Figure 9:
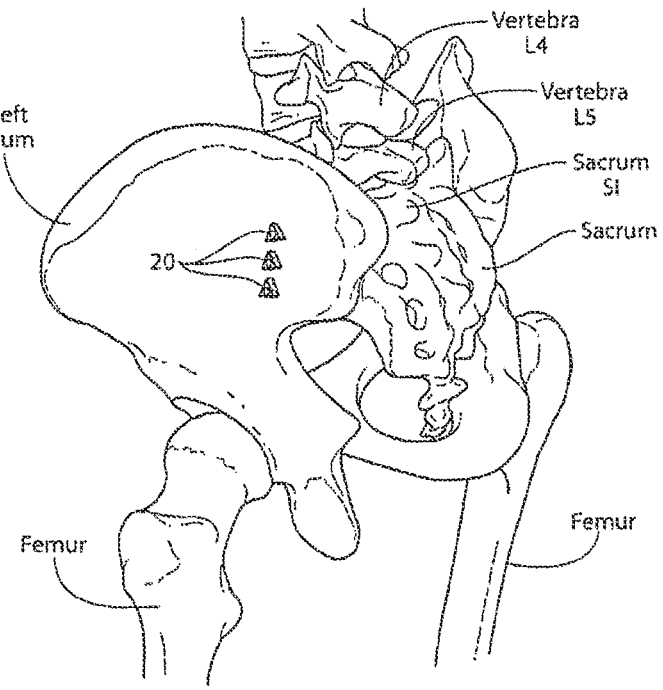
Figure 10:
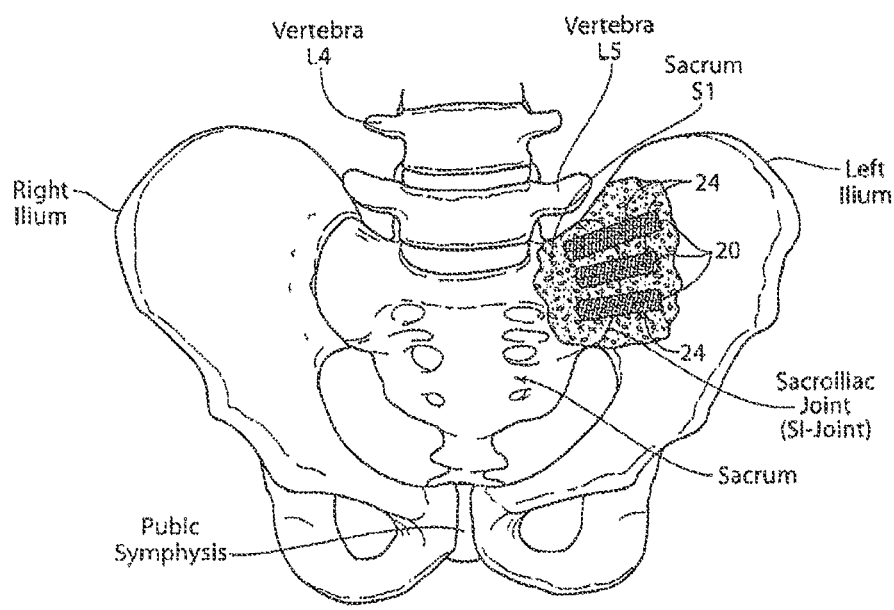

In this exemplary embodiment, one or more implant structures 20 are introduced laterally through the ilium, the SI-Joint, and into the sacrum. This path and resulting placement of the implant structure(s) 20 are best shown in FIGS. 9 and 10. In the illustrated embodiment, three implant structures 20 are placed in this manner. Also in the illustrated embodiment, the implant structures 20 are rectilinear in cross section and triangular in this case, but it should be appreciated that implant structures 20 of other rectilinear cross sections can be used. Additionally, in some procedures (not discussed in further detail herein), implants may be introduced into the SI-Joint from an anterior direction. Further information on anterior techniques may be found in co-pending U.S. patent application Pub. No. 2015/0105828 filed Oct. 15, 2014 and entitled "Implant Placement". The decortication instruments and methods disclosed herein and variants thereof may also be utilized in these anterior procedures.

Before undertaking a lateral implantation procedure, the physician diagnoses the SI-Joint segments that are to be fixated or fused (arthrodesed) using, e.g., the Fortin finger test, thigh thrust, FABER, Gaenslen's, compression, distraction, and or diagnostic SI-Joint injection.

Aided by lateral, inlet, and outlet C-arm views, and with the patient lying in a prone position, the physician aligns the greater sciatic notches and then the alae (using lateral visualization) to provide a true lateral position. A 3 cm incision is made starting aligned with the posterior cortex of the sacral canal, followed by blunt tissue separation to the ilium. From the lateral view, the guide pin 38 (with pin sleeve (not shown)) (e.g., a Steinmann Pin) is started resting on the ilium at a position inferior to the sacrum end plate and just anterior to the sacral canal. In the outlet view, the guide pin 38 should be parallel to the sacrum end plate at a shallow angle anterior (e.g., 15 degree to 20 degree off the floor, as FIG. 10 shows). In a lateral view, the guide pin 38 should be posterior to the sacrum anterior wall. In the outlet view, the guide pin 38 should be superior to the first sacral foramen and lateral of mid-line. This corresponds generally to the sequence shown diagrammatically in FIGS. 7A and 7B. A soft tissue protector (not shown), and a drill sleeve (not shown) within the soft tissue protector, may be slipped over the guide pin 38 and firmly against the ilium before removing the guide pin sleeve (not shown).

Figure 7A:
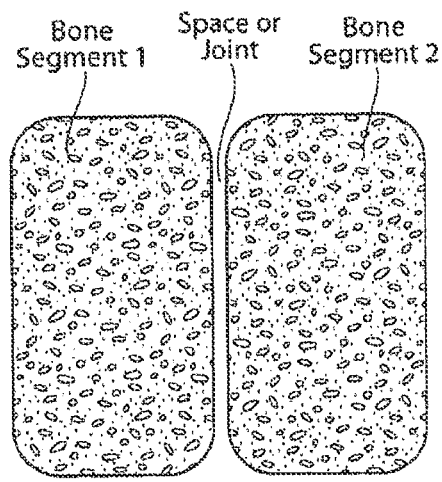
FIGS. 7A-7D are side section views of the formation of a broached bore in bone.
Figure 7B:
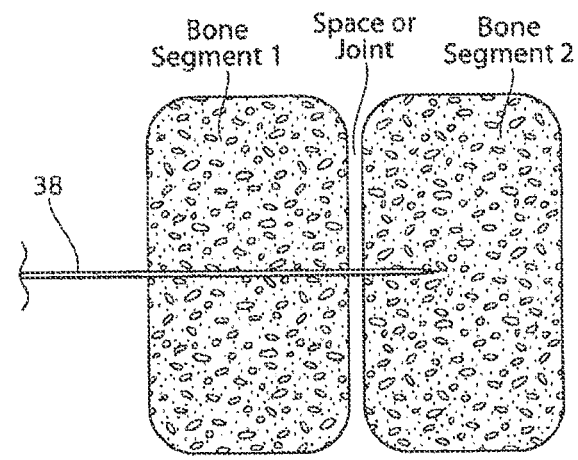
Figure 7C:
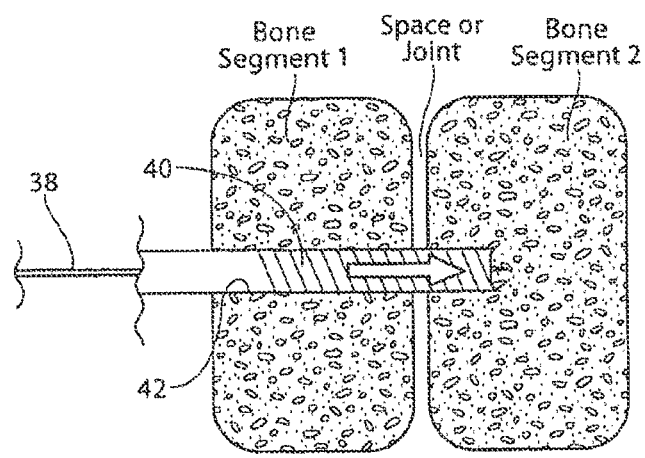
Figure 7D:
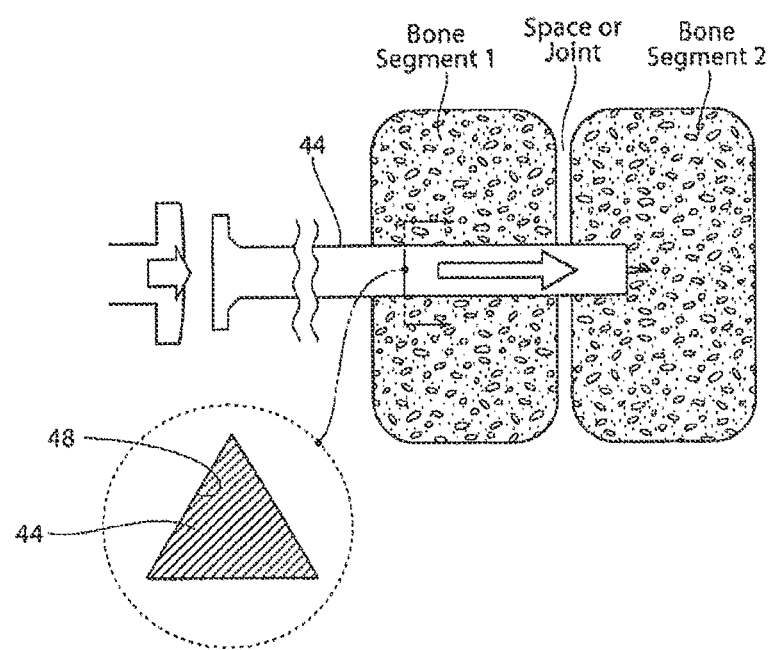

Over the guide pin 38 (and through the soft tissue protector and drill sleeve), a pilot bore 42 may be drilled with cannulated drill bit 40, as is diagrammatically shown in FIG. 7C. The pilot bore 42 may extend through the ilium, through the SI-Joint, and into the sacrum. The drill bit 40 and drill sleeve (not shown) are then removed.

Figure 8:
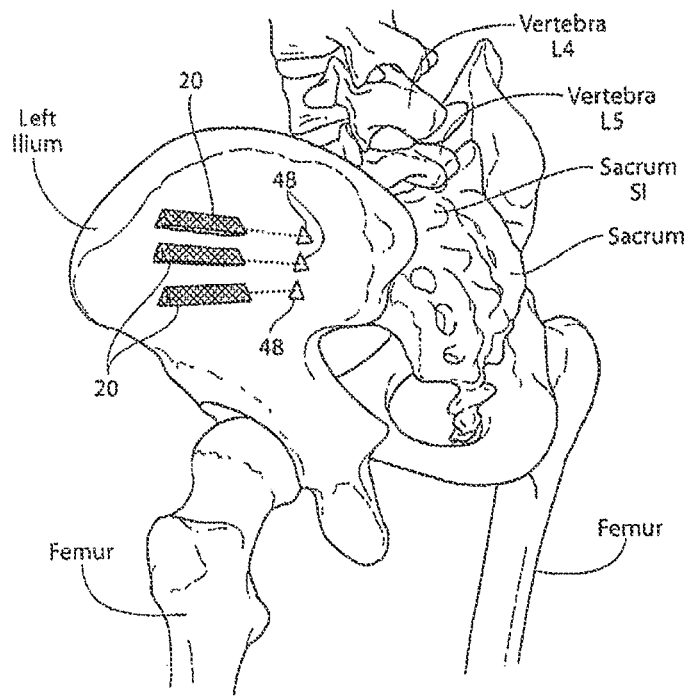
FIGS. 8 to 10 are anatomic views showing, respectively, a pre-implanted perspective, implanted perspective, and implanted anterior view, the implantation of three implant structures for the fixation of the SI-Joint using a lateral approach through the ilium, the SI-Joint, and into the sacrum.

A shaped broach 44 may be tapped into the pilot bore 42 over the guide pin 38 (and through the soft tissue protector, not shown) to create a broached bore 48 with the desired profile for the implant structure 20, which, in the illustrated embodiment, is triangular. This generally corresponds to the sequence shown diagrammatically in FIG. 7D. The triangular profile of the broached bore 48 is also shown in FIG. 8.

FIGS. 7E and 7F illustrate an embodiment of the assembly of a soft tissue protector or dilator or delivery sleeve 200 with a drill sleeve 202, a guide pin sleeve 204 and a handle 206. In some embodiments, the drill sleeve 202 and guide pin sleeve 204 can be inserted within the soft tissue protector 200 to form a soft tissue protector assembly 210 that can slide over the guide pin 208 until bony contact is achieved.

The soft tissue protector 200 can be any one of the soft tissue protectors or dilators or delivery sleeves disclosed herein. In some embodiments, an expandable dilator or delivery sleeve 200 can be used in place of a conventional soft tissue dilator. In the case of the expandable dilator, in some embodiments, the expandable dilator can be slid over the guide pin and then expanded before the drill sleeve 202 and/or guide pin sleeve 204 are inserted within the expandable dilator. In other embodiments, insertion of the drill sleeve 202 and/or guide pin sleeve 204 within the expandable dilator can be used to expand the expandable dilator.

In some embodiments, a dilator can be used to open a channel though the tissue prior to sliding the soft tissue protector assembly 210 over the guide pin. The dilator(s) can be placed over the guide pin, using for example a plurality of sequentially larger dilators or using an expandable dilator. After the channel has been formed through the tissue, the dilator(s) can be removed and the soft tissue protector assembly can be slid over the guide pin. In some embodiments, the expandable dilator can serve as a soft tissue protector after being expanded. For example, after expansion the drill sleeve and guide pin sleeve can be inserted into the expandable dilator.

As shown in FIGS. 8 and 9, a triangular implant structure 20 can be now tapped through the soft tissue protector over the guide pin 38 through the ilium, across the SI-Joint, and into the sacrum, until the proximal end of the implant structure 20 is flush against the lateral wall of the ilium (see also FIGS. 5 and 10). The guide pin 38 and soft tissue protector are withdrawn, leaving the implant structure 20 residing in the broached passageway, flush with the lateral wall of the ilium (see FIGS. 5 and 10). In the illustrated embodiment, two additional implant structures 20 are implanted in this manner, as FIG. 9 best shows. In other embodiments, the proximal ends of the implant structures 20 are left proud of the lateral wall of the ilium, such that they extend 1, 2, 3 or 4 mm outside of the ilium. This ensures that the implants 20 engage the hard cortical portion of the ilium rather than just the softer cancellous portion, through which they might migrate if there was no structural support from hard cortical bone. The hard cortical bone can also bear the loads or forces typically exerted on the bone by the implant 20.

The implant structures 20 are sized according to the local anatomy. For the SI-Joint, representative implant structures 20 can range in size, depending upon the local anatomy, from about 35 mm to about 60 mm in length, and about a 7 mm inscribed diameter (i.e. a triangle having a height of about 10.5 mm and a base of about 12 mm). The morphology of the local structures can be generally understood by medical professionals using textbooks of human skeletal anatomy along with their knowledge of the site and its disease or injury. The physician is also able to ascertain the dimensions of the implant structure 20 based upon prior analysis of the morphology of the targeted bone using, for example, plain film x-ray, fluoroscopic x-ray, or MRI or CT scanning.

Using a lateral approach, one or more implant structures 20 can be individually inserted in a minimally invasive fashion across the SI-Joint, as has been described. Conventional tissue access tools, obturators, cannulas, and/or drills can be used for this purpose. Alternatively, the novel tissue access tools described above and in U.S. Provisional Patent Application No. 61/609,043, titled "TISSUE DILATOR AND PROTECTOR" and filed Mar. 9, 2012, and in U.S. Published Application No. 2017/0007409, titled "SYSTEMS, DEVICES, AND METHODS FOR JOINT FUSION" and filed Jul. 12, 2016, can also be used. No joint preparation, removal of cartilage, or scraping are required before formation of the insertion path or insertion of the implant structures 20, so a minimally invasive insertion path sized approximately at or about the maximum outer diameter of the implant structures 20 can be formed.

The implant structures 20 can obviate the need for autologous bone graft material, additional pedicle screws and/or rods, hollow modular anchorage screws, cannulated compression screws, threaded cages within the joint, or fracture fixation screws. Still, in the physician's discretion, bone graft material and other fixation instrumentation can be used in combination with the implant structures 20.

In a representative procedure, one to six, or perhaps up to eight, implant structures 20 can be used, depending on the size of the patient and the size of the implant structures 20. After installation, the patient would be advised to prevent or reduce loading of the SI-Joint while fusion occurs. This could be about a six to twelve week period or more, depending on the health of the patient and his or her adherence to post-op protocol.

The implant structures 20 make possible surgical techniques that are less invasive than traditional open surgery with no extensive soft tissue stripping. The lateral approach to the SI-Joint provides a straightforward surgical approach that complements the minimally invasive surgical techniques. The profile and design of the implant structures 20 minimize or reduce rotation and micromotion. Rigid implant structures 20 made from titanium provide immediate post-op SI-Joint stability. A bony in-growth region 24 comprising a porous plasma spray coating with irregular surface supports stable bone fixation/fusion. The implant structures 20 and surgical approaches make possible the placement of larger fusion surface areas designed to maximize post-surgical weight bearing capacity and provide a biomechanically rigorous implant designed specifically to stabilize the heavily loaded SI-Joint. In some embodiments, a fenestrated matrix implant may be used, providing cavities in which to pack bone growth material, and or providing additional surface area for bone on-growth, in-growth and or through-growth.

To improve the stability and weight bearing capacity of the implant, the implant can be inserted across three or more cortical walls. For example, after insertion the implant can traverse two cortical walls of the ilium and at least one cortical wall of the sacrum. The cortical bone is much denser and stronger than cancellous bone and can better withstand the large stresses found in the SI-Joint. By crossing three or more cortical walls, the implant can spread the load across more load bearing structures, thereby reducing the amount of load borne by each structure. In addition, movement of the implant within the bone after implantation is reduced by providing structural support in three locations around the implant versus two locations.

Further details of bone joint implants and methods of use can be found in U.S. Pat. No. 8,308,779 entitled "SYSTEMS AND METHODS FOR THE FIXATION OR FUSION OF BONE" filed Feb. 25, 2008, U.S. Pat. No. 7,922,765 entitled "SYSTEMS AND METHODS FOR THE FIXATION OR FUSION OF BONE" filed Mar. 24, 2005, U.S. Pat. No. 8,986,348 entitled "SYSTEMS AND METHODS FOR THE FUSION OF THE SACRAL-ILIAC JOINT" filed Oct. 5, 2010, and U.S. Pat. No. 8,414,648 entitled "APPARATUS, SYSTEMS, AND METHODS FOR ACHIEVING TRANS-ILIAC LUMBAR FUSION" filed Dec. 6, 2010

In the previously described methods, the implant(s) 10 or 20 (FIGS. 3 and 4) may be placed in the implant bore(s) 48 (FIG. 8) using a generally medial or axial, non-rotational force, such as tapping an implant into place using a slide hammer. In other embodiments, according to aspects of the present disclosure, the implant(s) may comprise external threads and may be threaded into place by applying a rotational force, as will now be described.

Figure 11:
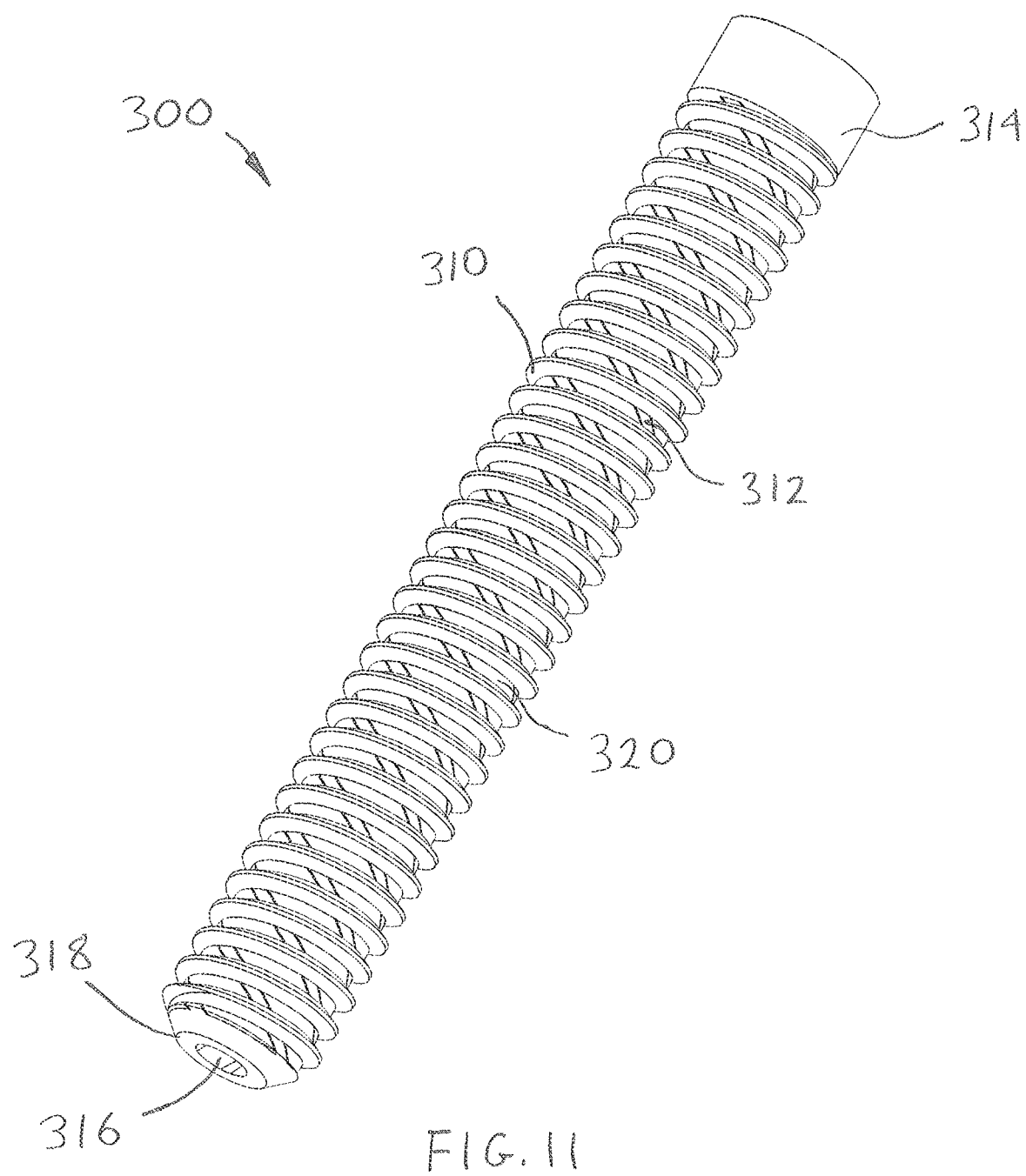
FIG. 11 is a perspective view showing an exemplary embodiment of a threaded implant constructed according to aspects of the present disclosure.
Figure 12:
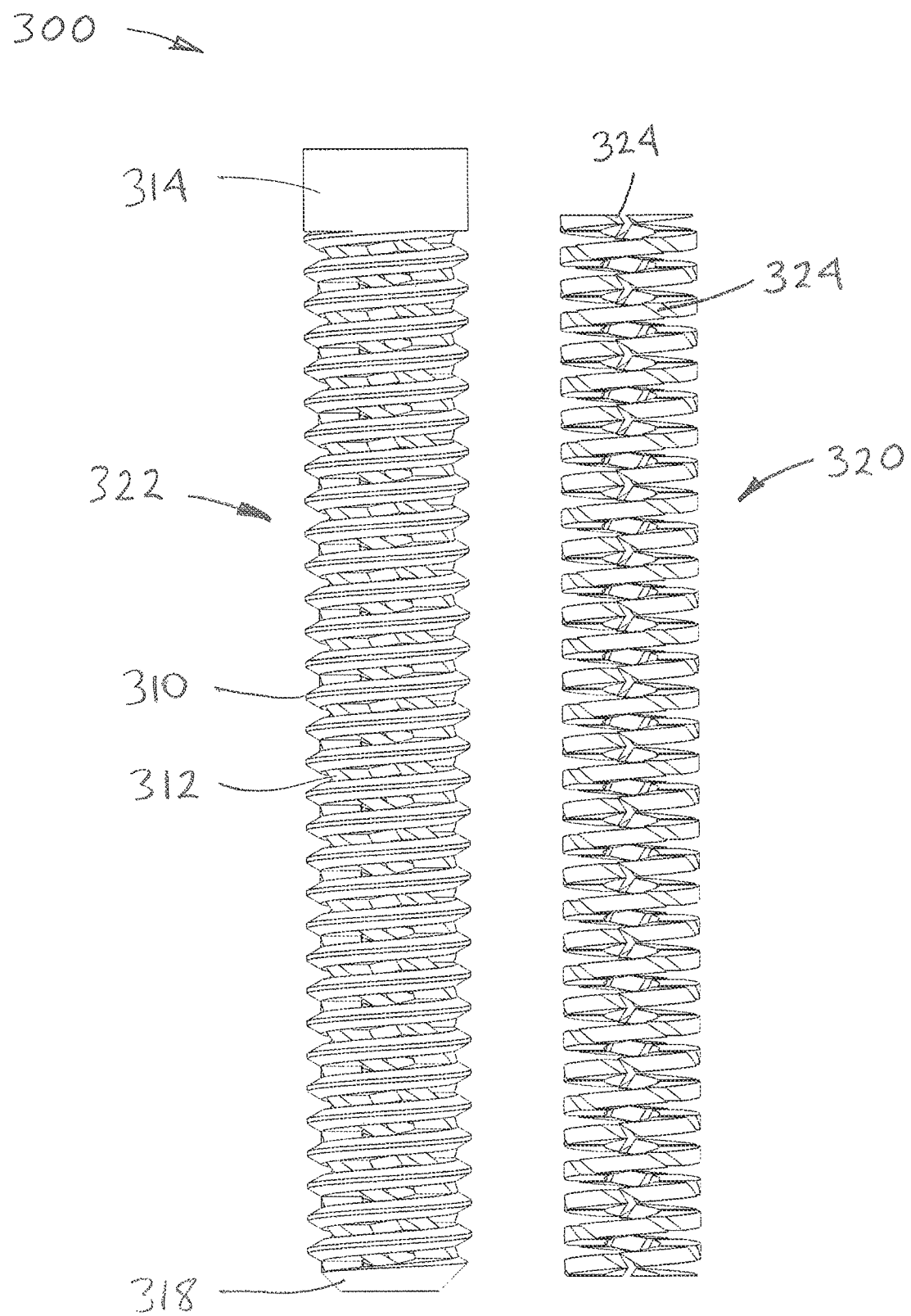
FIG. 12 is a side elevation exploded view of the implant shown in FIG. 11.
Figure 13:
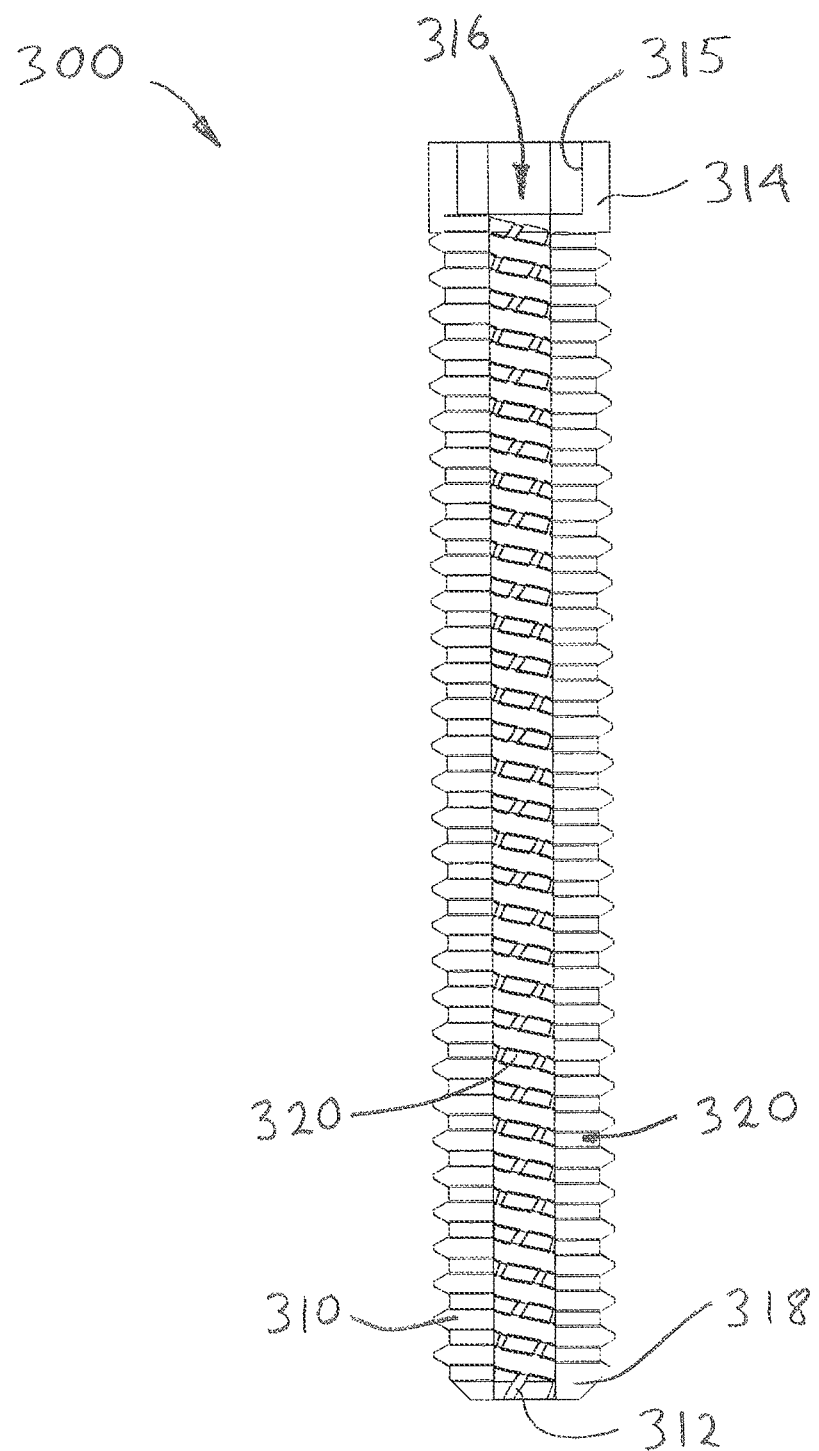
FIG. 13 is a side elevation cross-sectional view of the implant shown in FIG. 11.

Referring to FIGS. 11-13, an exemplary embodiment of a threaded implant system constructed according to aspects of the present disclosure is shown. Implant 300 is provided with external threads 310 and an internal counter-rotating support structure 312. As best seen in FIG. 13, proximal end 314 may be provided with a hexagonally shaped socket 315 for receiving a drive tool (not shown) when implant 300 is being inserted or removed. A through bore 316 may be provided along the central axis from the proximal end 314 to the distal end 318.

External threads 310 are used to engage bone when threading implant 300 across a bone joint. In some embodiments, external threads 310 are self-tapping. In this embodiment, internal counter-rotating support structure 312 extends helically in an opposite direction from external threads 310 as shown. Support structure 312 provides stiffness and torsional rigidity to implant 300 while permitting fenestrations between external threads 310 for promoting better bony on-growth, ingrowth and/or through-growth. In this exemplary embodiment, a single external thread 310 helically extends from near the proximal end 314 to the distal end 318 of implant 300. In other embodiments (not shown), multiple starts of external threads 310 may be employed. In this embodiment, internal counter-rotating support structure 312 comprises four starts. In other embodiments (not shown), fewer or more starts may be employed. In this embodiment, internal counter-rotating support structure 312 has a pitch that is eight times the pitch of external threads 310. In other embodiments (not shown), the pitch of structure 312 may be less or more than eight times that of threads 310. In other embodiments (not shown), support structure 312 may extend in the same direction as external threads 310 rather than counter-rotating relative to it, and or may form a shape other than helical. Support structure 312 may comprise layers. In some embodiments, these layers alternate in direction.

In the exemplary embodiment of FIGS. 11-13, the fenestrations or interstices between external threads 310 and internal counter-rotating support structure 312 are filled with porous infill 320. Infill 320 provides scaffolding with a large surface area for new bone growth. Infill 320 can also add additional strength to implant 300 in compression, tension, torsion, bending, shear, etc., but still allow for better bony on-growth, ingrowth and/or through-growth than if the fenestrations or interstices were completely filled with less porous material. The exploded view of FIG. 12 shows main portion 322 of implant 300 separately from the porous infill 320 for clarity, although in this embodiment infill 320 is a collection of many individual segments rather than an interconnected structure. In some embodiments, main portion 322 may also be porous, but having a different porosity than infill 320. For example, infill 320 may be at least 20% more porous than main portion 322. Both may be made together in the same manufacturing process, such as 3D printing or other additive manufacturing process. In some embodiments, infill 320 is formed from the same material as main portion 322, while in other embodiments a different material or materials may be used to form infill 320.

In some embodiments, porous infill 320 has the same inner diameter as that of the main portion 322 of implant 300, forming a continuous surface defining through bore 316, as shown in FIG. 13. The outer diameter of infill 320 may be the same diameter of the radially inward end of the tapered portions of threads 310, thereby forming the root diameter of threads 310. The inner and outer diameters of counter-rotating support structure 312 may also be the same as those of infill 320, such that breaks 324 are formed in infill 320 (as seen in FIG. 12) to accommodate structure 312.

An implant bore may be formed across a bone segment before implant 300 is threaded into it. In some embodiments the diameter of the bore is approximately the same as the root diameter of threads 310. In some embodiments, a tap may be used to create internal threads inside the bone before implant 300 is inserted. In other embodiments, self-boring and/or self-tapping features are provided on implant 300. Implant 300 may be threaded into the bore until just the proximal head portion protrudes from the bone. In other implementations, proximal head portion may be partially or fully recessed into the bone, or flush with the outer surface of the bone.

Figure 14:
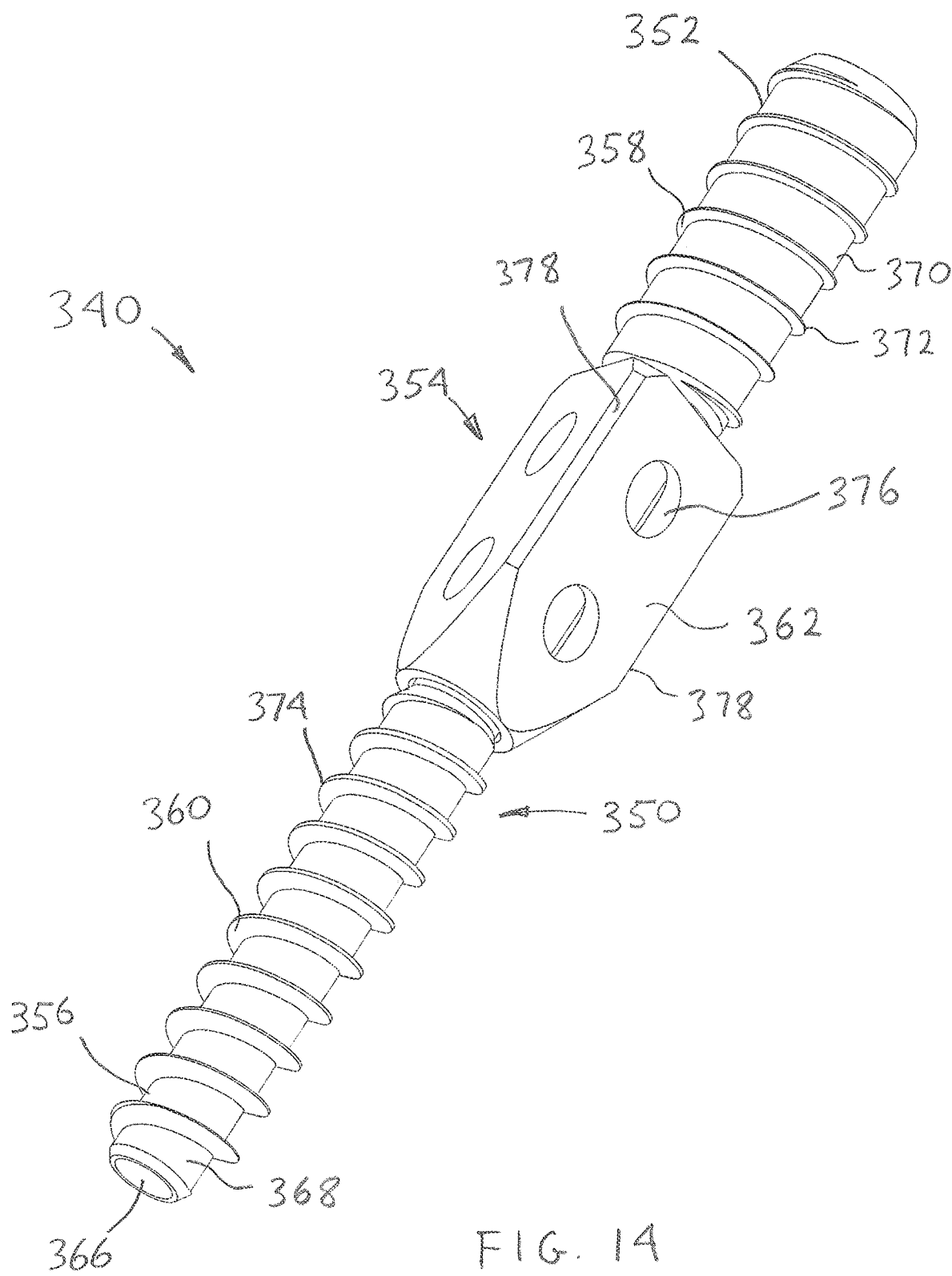
FIG. 14 is a perspective view showing another exemplary embodiment of a threaded implant constructed according to aspects of the present disclosure.

Referring to FIGS. 14-17, another exemplary embodiment of a threaded implant system constructed according to aspects of the present disclosure is shown. Implant 340 comprises a main body 350 having a proximal end 352, a mid-section 354 and a distal end 356. Proximal end 352 is provided with a first set of threads 358 while distal end 356 is provided with a second set of threads 360. As best seen in the exploded view of FIG. 15, mid-section 354 has a constant diameter configured to receive triangle sleeve 362 (as shown in FIG. 14) such that it may rotate with respect to main body 350 while being constrained from axial movement.

Figure 16:
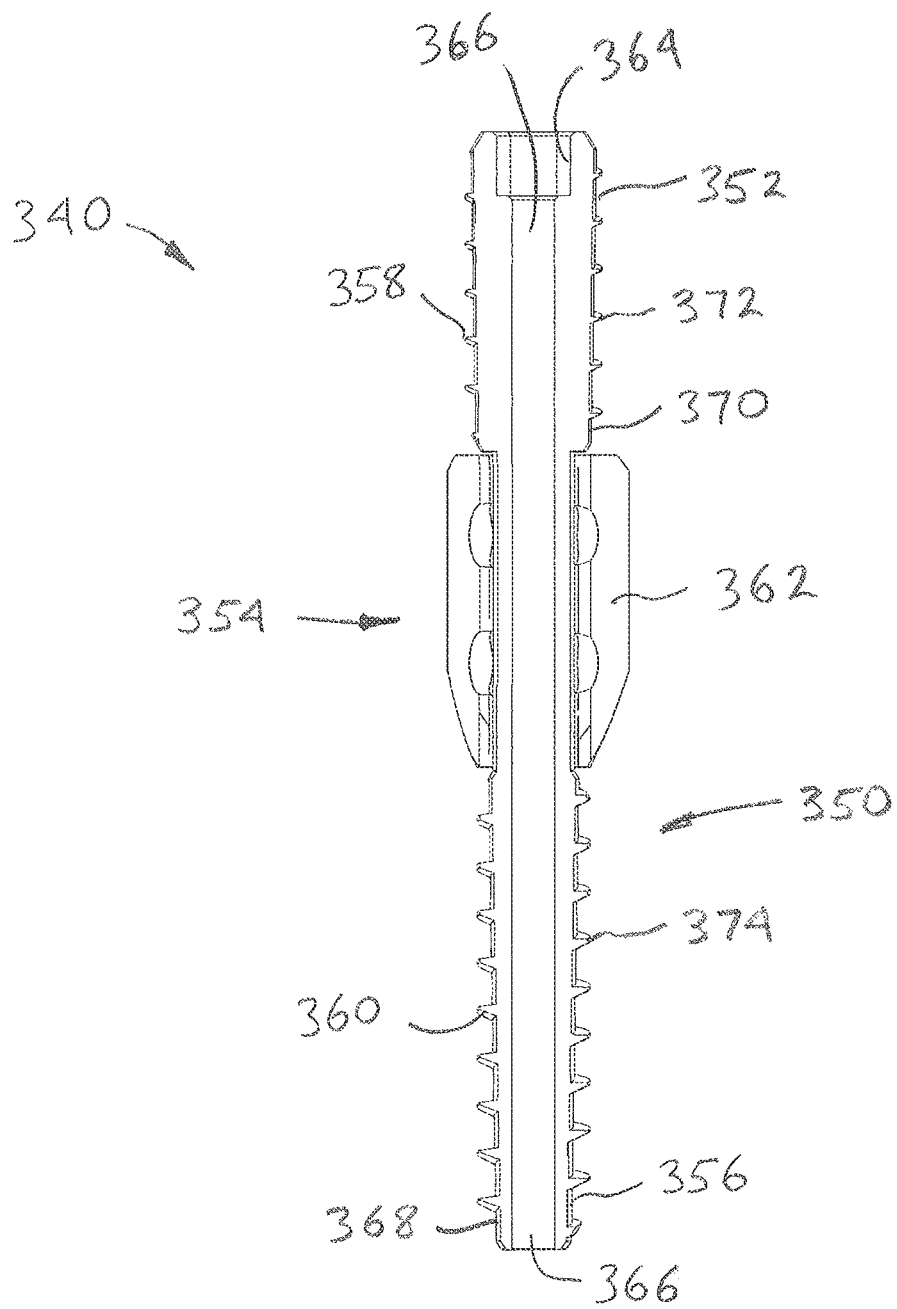
FIG. 16 is a side elevation cross-sectional view of the implant shown in FIG. 14.

Referring to FIG. 16, proximal end 352 of main body 350 may be provided with a hexagonally shaped socket 364 for receiving a drive tool (not shown) when implant 340 is being inserted or removed. A through bore 366 may be provided along the central axis from the proximal end 352 to the distal end 356. As also shown in FIG. 16, main body 350 may be provided with a constant root or minor diameter taper that extends from a smaller diameter 368 at distal end 356 to a larger diameter 370 closer to proximal end 352, except for mid-section 354 which has a smaller diameter than the tapered root or minor diameter sections adjacent to it. The first set of threads 358 may have a constant outer or major diameter 372, such that threads 358 protrude radially less from the root or minor diameter as they extend proximally along main body as shown in FIG. 16. Similarly, the second set of threads 360 may have a constant outer or major diameter 374 (larger than the outer or major diameter 372 of the first set of threads 358), such that threads 360 protrude radially less from the root or minor diameter as they extend proximally along main body as shown in FIG. 16.

In some variations of this embodiment (not shown), the pitch of distal threads 360 is greater than the pitch of proximal threads 372. This arrangement causes implant 340 to advance more rapidly in relation to a distal bone segment that it does relative to a more proximal bone segment, thereby drawing the two bone segments closer together (e.g. compressing a joint between the two bone segments) when the implant is tightened into place.

Figure 15:
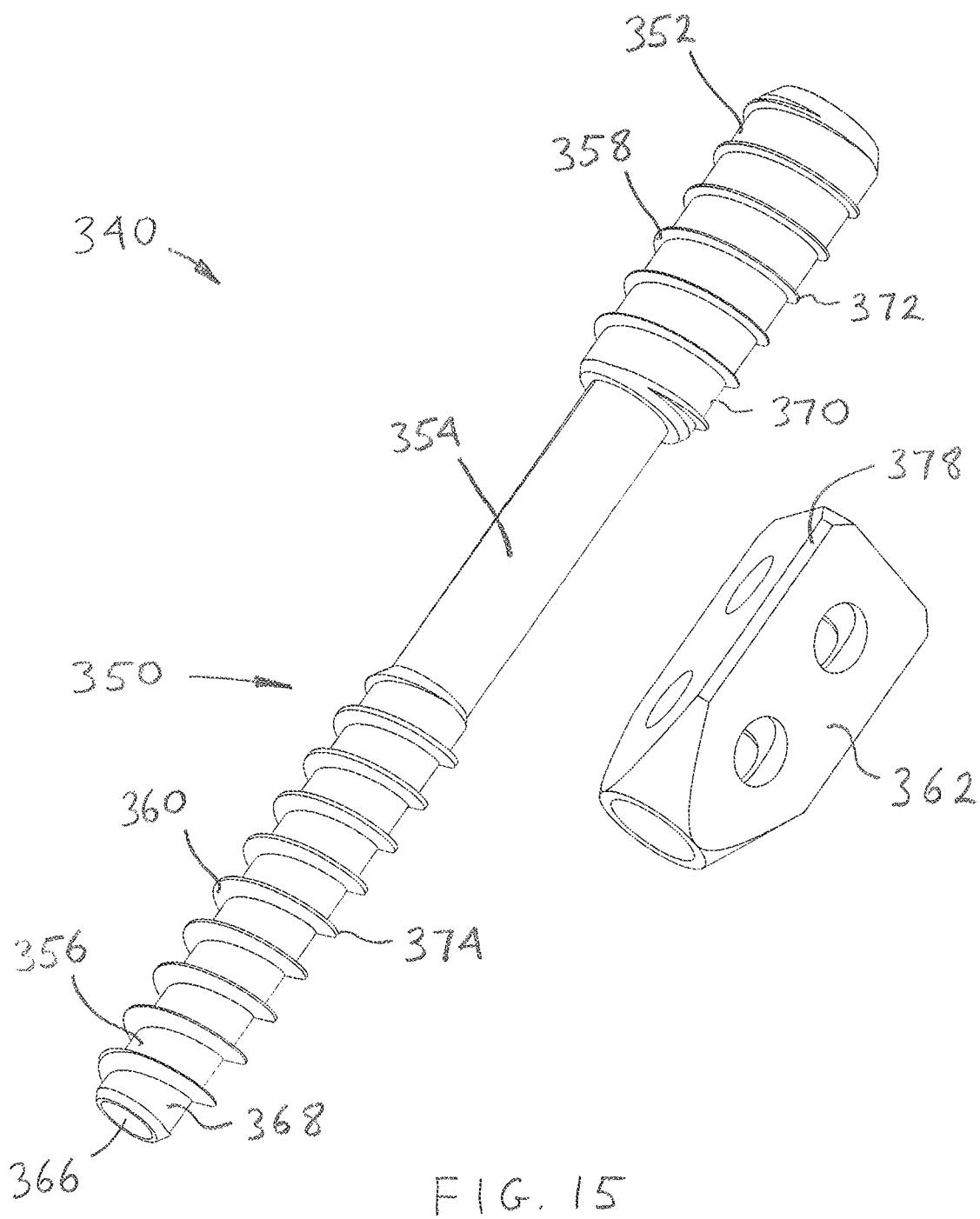
FIG. 15 is a perspective exploded view of the implant shown in FIG. 14.

Referring to FIGS. 14 and 15, one or more fenestrations 376 may be provided in triangle sleeve 362 such that they communicate with a space around mid-section 354. Fenestrations 376 provide additional area for on-growth, ingrowth and through-growth of new bone tissue after implantation of device 340. During implantation, bone chips may be placed inside fenestrations 376 to aid in new bone growth. Chamfers 378 (also shown in FIG. 17) may be provided along the apexes of triangle sleeve 362. One advantage to providing chamfers 378 is that stress concentrations are avoided when creating a bore through the bone for implant 340 to reside in.

Figure 17:
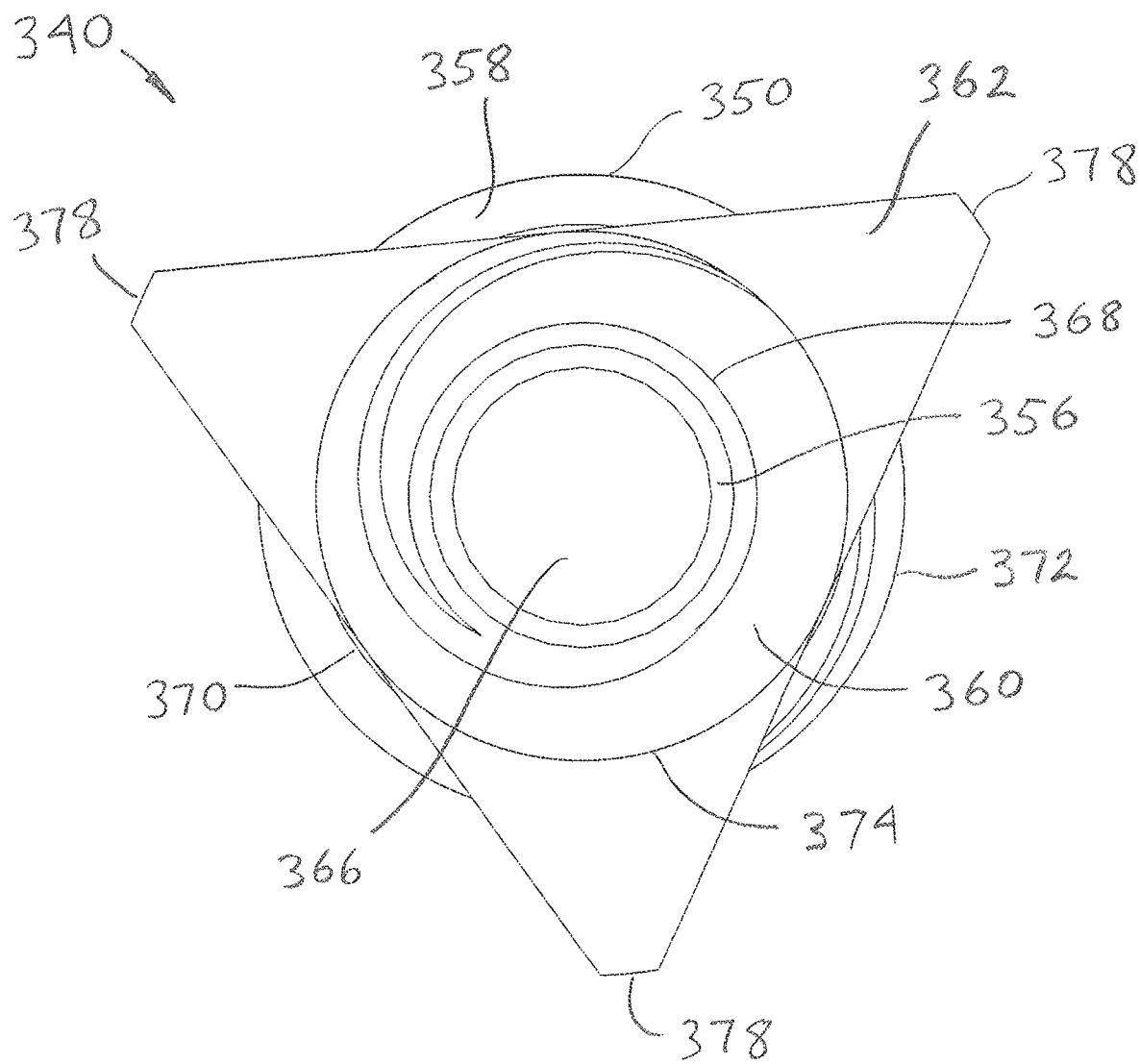
FIG. 17 is a distal end view of the implant shown in FIG. 14.

Device 340 may be implanted in bone in a manner similar to previously described embodiments. Triangle sleeve 362 may be provided with tapered leading edges (as shown in FIG. 14), self-broaching features (not shown), and/or a separate broaching instrument (not shown) may be used to create a triangularly shaped bore before device 340 is implanted. In some embodiments, triangle sleeve 362 resides across a gap between two bone segments once device 340 is in place. A triangularly shaped bore may be broached just deep enough to accommodate triangle sleeve 362, but not all the way to the distal tip of device 340. In some embodiments, the full depth of threads 358 extends beyond the flats of triangle sleeve 362 and into the surrounding bone, as depicted in FIG. 17. During implantation, triangle sleeve 362 may freely rotate with respect to main body 350 such that it travels axially into the triangularly shaped bore in the bone without rotating while main body 350 is rotated and advances with threads 360 and 358. In some embodiments, bone in-growth and through-growth after implantation causes triangle sleeve 362 to become rigid with main body 350. This mechanism inhibits implant 340 from backing out of the bone or migrating further into it, since triangle sleeve 362 is prevented from rotating by the surrounding triangularly shaped bore in the bone. In some embodiments (not shown), a mechanism such as a toggle, cam, or other feature can be activated immediately after implantation to lock triangle sleeve 362 to main body 350, thereby providing immediate anti-rotation.

Figure 18:
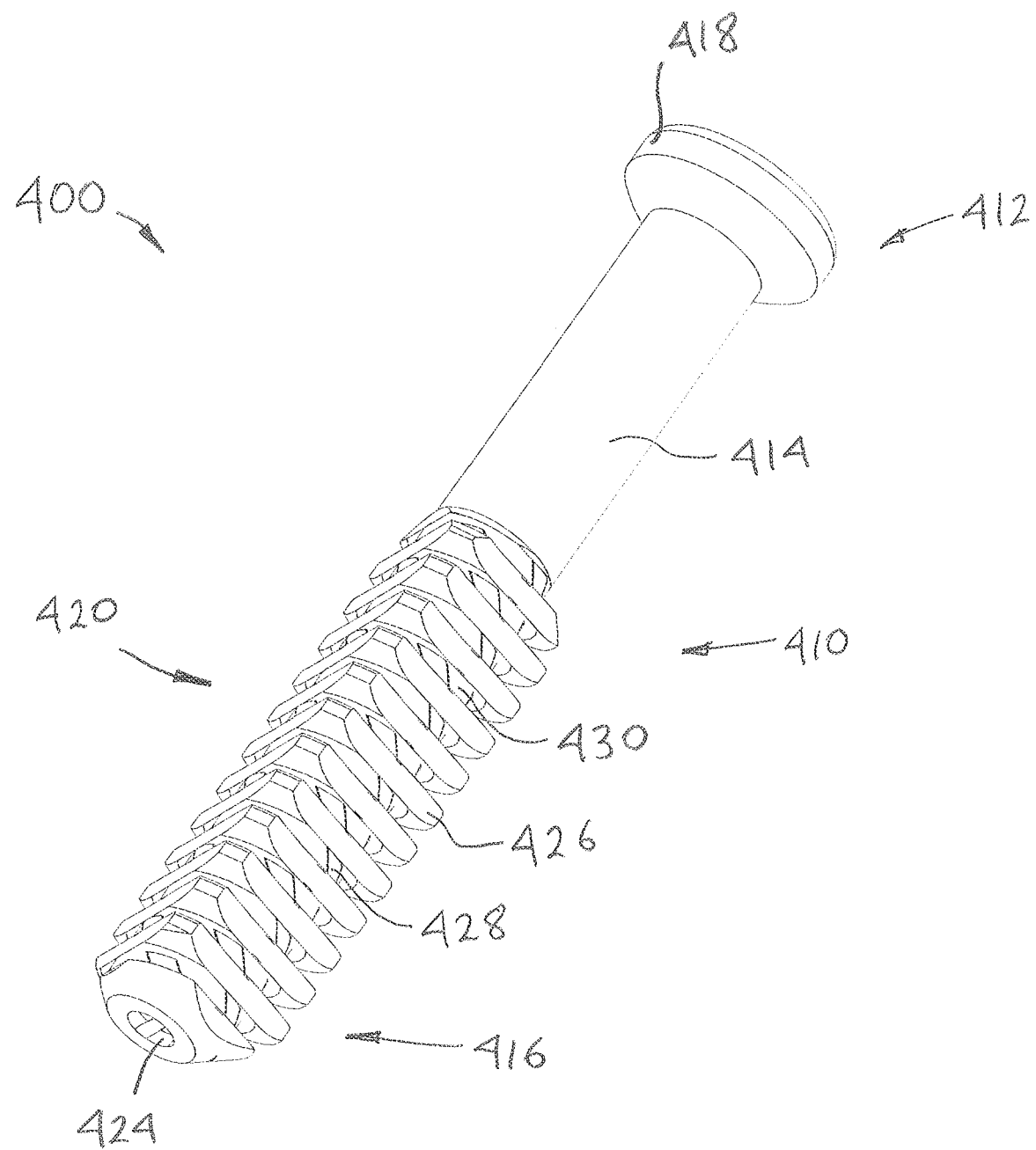
FIG. 18 is a perspective view showing another exemplary embodiment of a threaded implant constructed according to aspects of the present disclosure.
Figure 19:
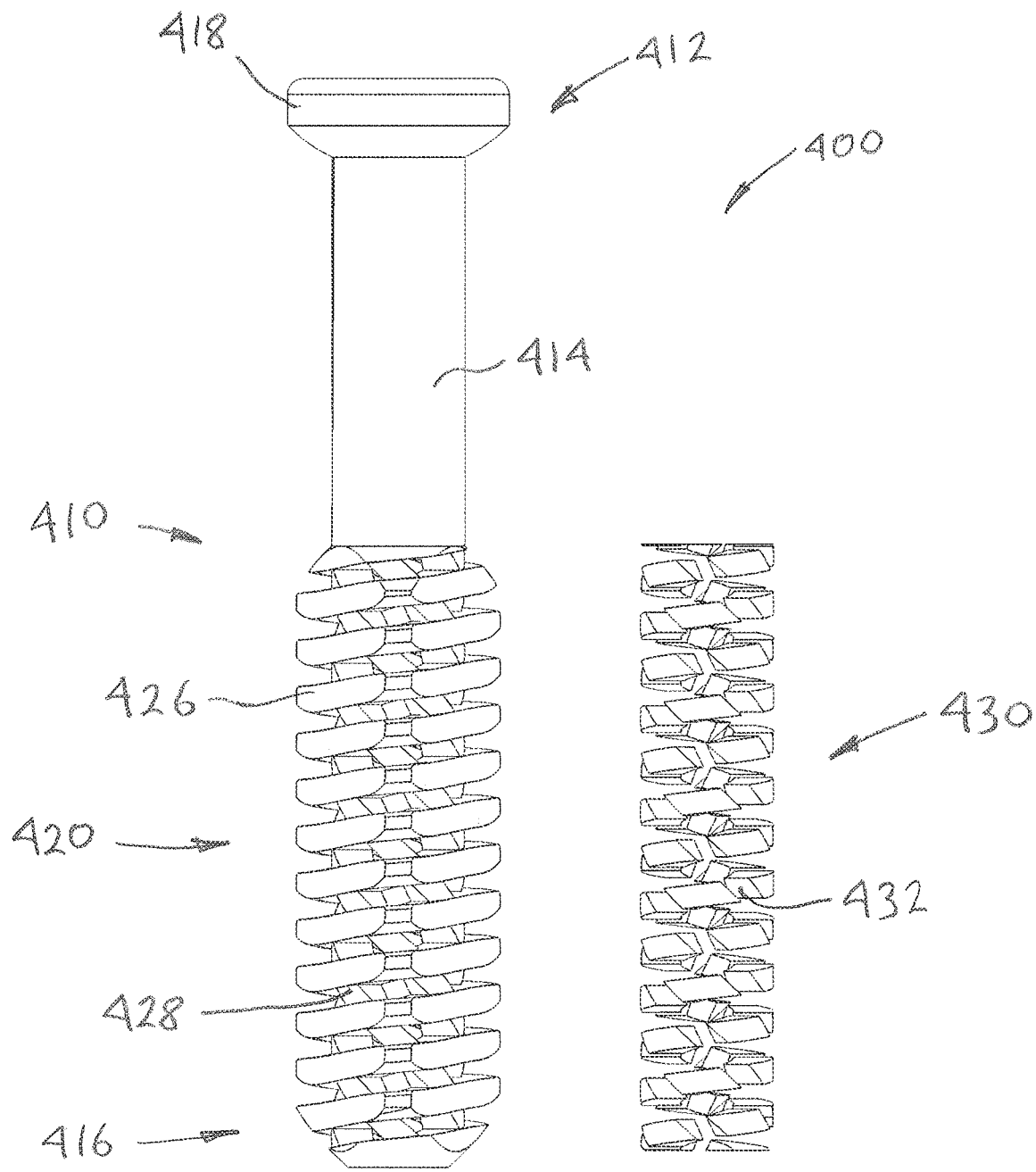
FIG. 19 is a side elevation exploded view of the implant shown in FIG. 18.
Figure 20:
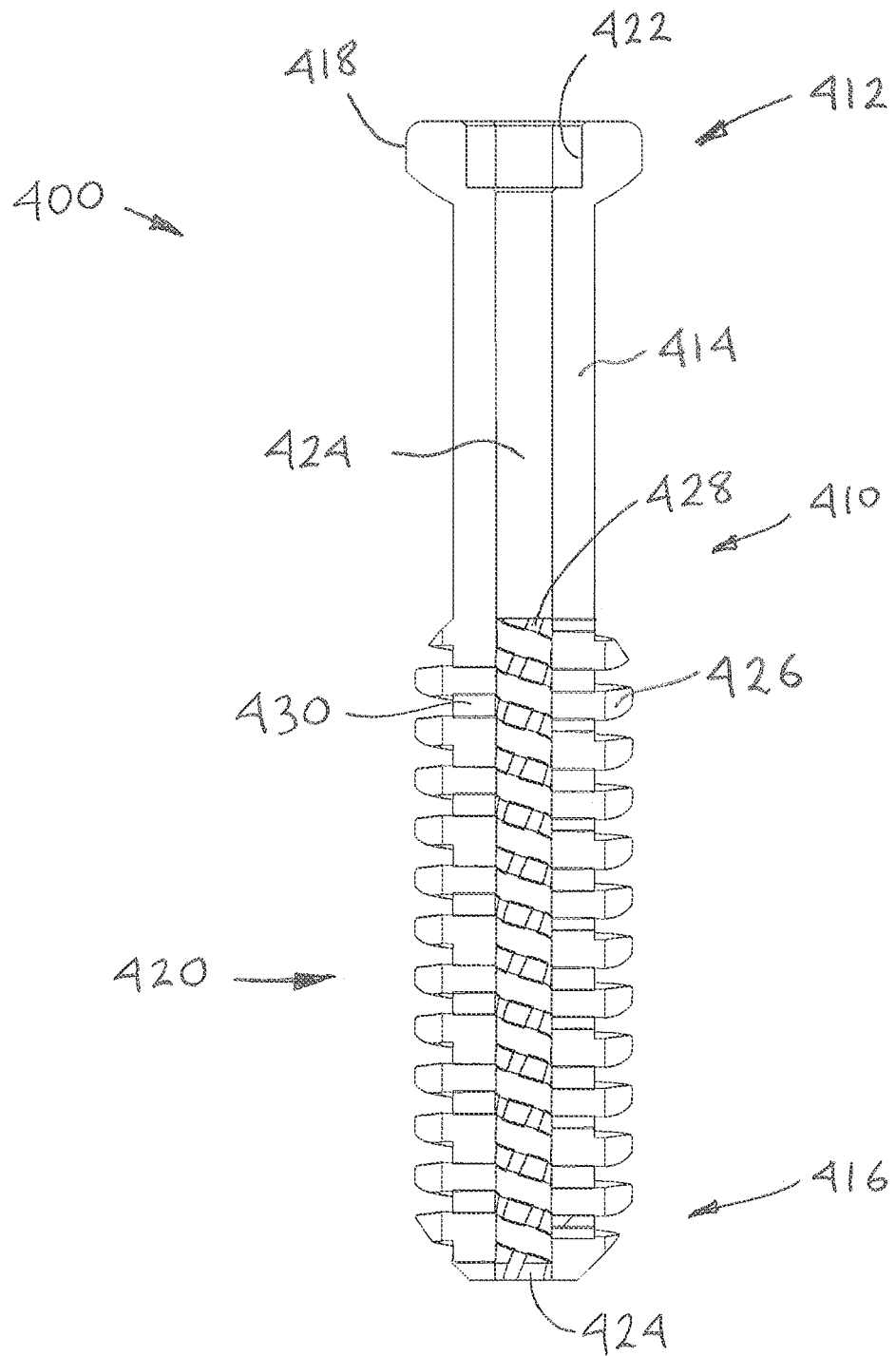
FIG. 20 is a side elevation cross-sectional view of the implant shown in FIG. 18.
Figure 21:
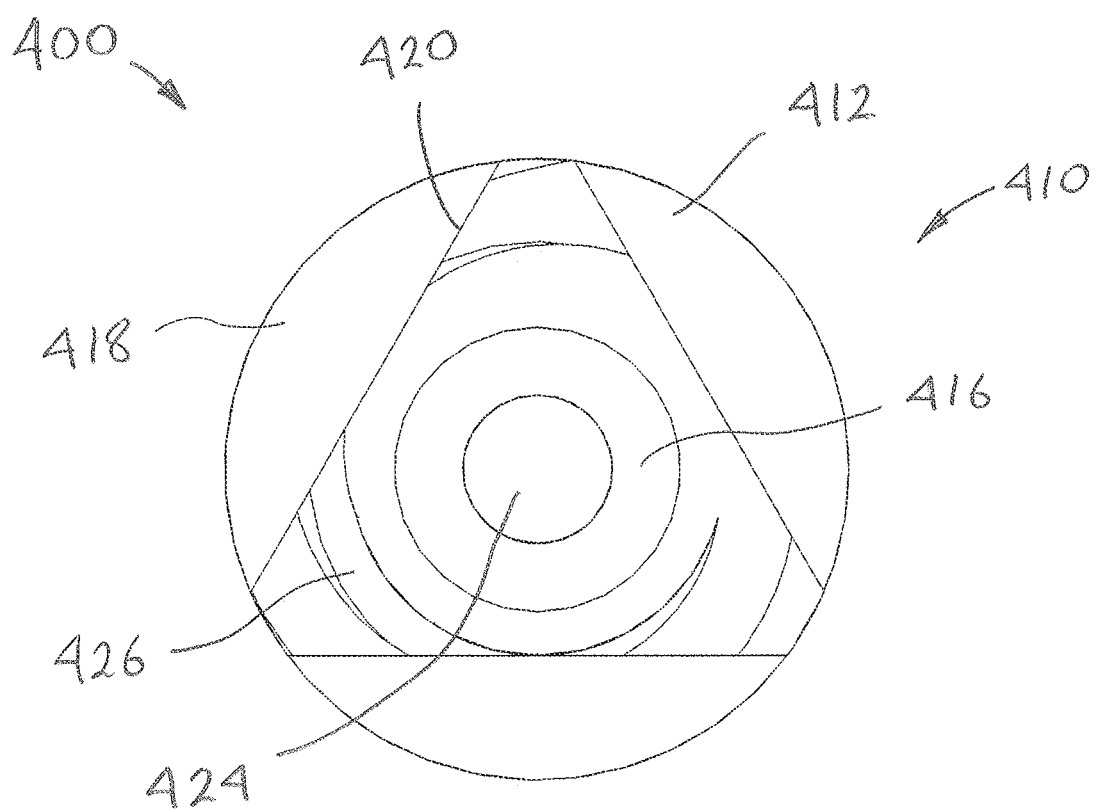
FIG. 21 is a distal end view of the implant shown in FIG. 18.

Referring to FIGS. 18-21, another exemplary embodiment of a threaded implant system constructed according to aspects of the present disclosure is shown. Implant 400 comprises a main body 410 having a proximal end 412, a mid-section 414 and a distal end 416. Proximal end 412 is provided with a head portion 418 configured to abut against an outer surface of a bone segment when implant 400 is implanted therein. Distal end 416 is provided with a threaded portion 420 having a triangular cross-section, as best seen in FIGS. 18 and 21. Mid-section 414 may have a constant diameter that extends radially to the same extent as the flat portions of the triangular cross-section. As shown in FIG. 20, proximal end 412 may be provided with a hexagonally shaped socket 422 for receiving a drive tool (not shown) when implant 400 is being inserted or removed. A through bore 424 may be provided along the central axis from the proximal end 412 to the distal end 416.

Similar to previously described implant 300 of FIGS. 11-13, threaded portion 420 of implant 400 is provided with external threads 426 and an internal counter-rotating support structure 428. External threads 426 are used to engage bone when threading implant 400 across a bone joint. In some embodiments, external threads 426 are self-tapping. In this embodiment, internal counter-rotating support structure 428 extends helically in an opposite direction from external threads 426 as shown. Support structure 428 provides stiffness and torsional rigidity to implant 400 while permitting fenestrations between external threads 426 for promoting better bony on-growth, ingrowth and/or through-growth. In this exemplary embodiment, a single external thread 426 helically extends from near the distal end 416 to the mid-section 414 of implant 400, although the thread is interrupted and has portions removed by the flat sides of the triangular cross-section. In other embodiments (not shown), multiple starts of external threads 426 may be employed. In this embodiment, internal counter-rotating support structure 428 comprises four starts. In other embodiments (not shown), fewer or more starts may be employed. In this embodiment, internal counter-rotating support structure 428 has a pitch that is eight times the pitch of external threads 426. In other embodiments (not shown), the pitch of structure 428 may be less or more than eight times that of threads 426, and or may form a shape other than helical.

Also similar to previously described implant 300 of FIGS. 11-13, the fenestrations or interstices of implant 400 between external threads 426 and internal counter-rotating support structure 428 are filled with porous infill 430. Infill 430 provides scaffolding with a large surface area for new bone growth. Infill 430 can also add additional strength to implant 400 in compression, tension, torsion, bending, shear, etc., but still allow for better bony on-growth, ingrowth and/or through-growth than if the fenestrations or interstices were completely filled with less porous material. The exploded view of FIG. 19 shows threaded portion 420 of implant 400 separately from the porous infill 430 for clarity, although in this embodiment infill 430 is a collection of many individual segments rather than an interconnected structure. In some embodiments, threaded portion 420 may also be porous, but having a different porosity than infill 430, as previously described. Both may be made together in the same manufacturing process, such as 3D printing or other additive manufacturing process.

In some embodiments, porous infill 430 has the same inner diameter as that of through bore 424, forming a continuous inner surface as shown in FIG. 20. The outer diameter of infill 430 may be the same diameter of the radially inward end of the tapered portions of threads 426, thereby forming the root diameter of threads 426. In this embodiment, these diameters are also equal to the outer diameter of mid-section 414. The inner and outer diameters of counter-rotating support structure 428 may also be the same as those of infill 430, such that breaks 432 are formed in infill 430 (as seen in FIG. 19) to accommodate structure 428.

In some embodiments, the implant site may be prepared by forming a round bore into the bone having a diameter approximately equal to the root diameter of threads 426. Implant 400 may be provided with self-boring and/or self-tapping features. Implant 400 may be implanted by inserting a hexagonal driver (not shown) into socket 422 and rotating implant 400 until head portion 418 contacts, becomes flush with or recessed within the outer bone surface. Bone chips may be packed into through bore 424 to aid in bone growth to further secure implant 400 as it heals in place.

Figure 22:
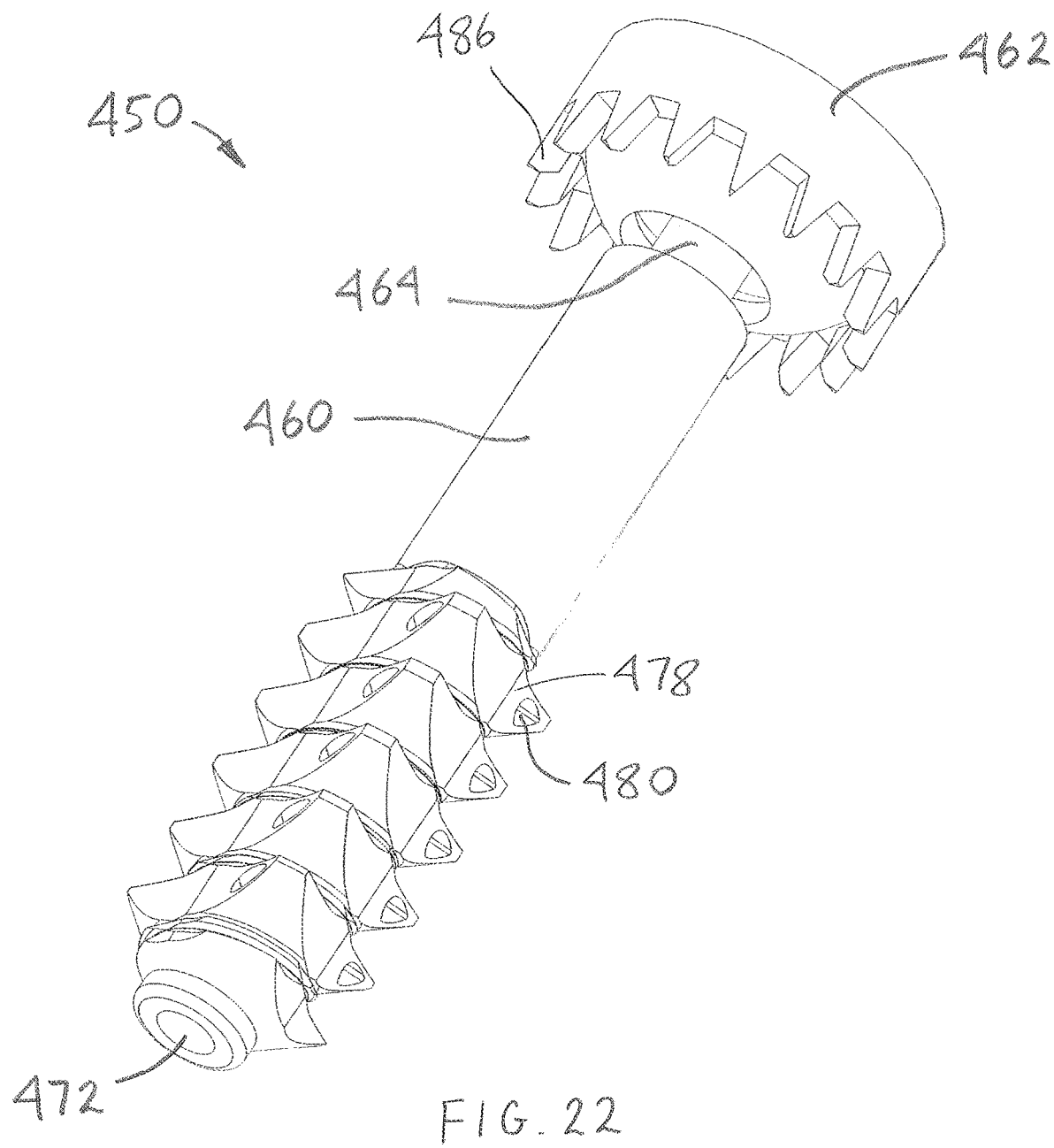
FIG. 22 is a perspective view showing another exemplary embodiment of a threaded implant constructed according to aspects of the present disclosure.
Figure 23:
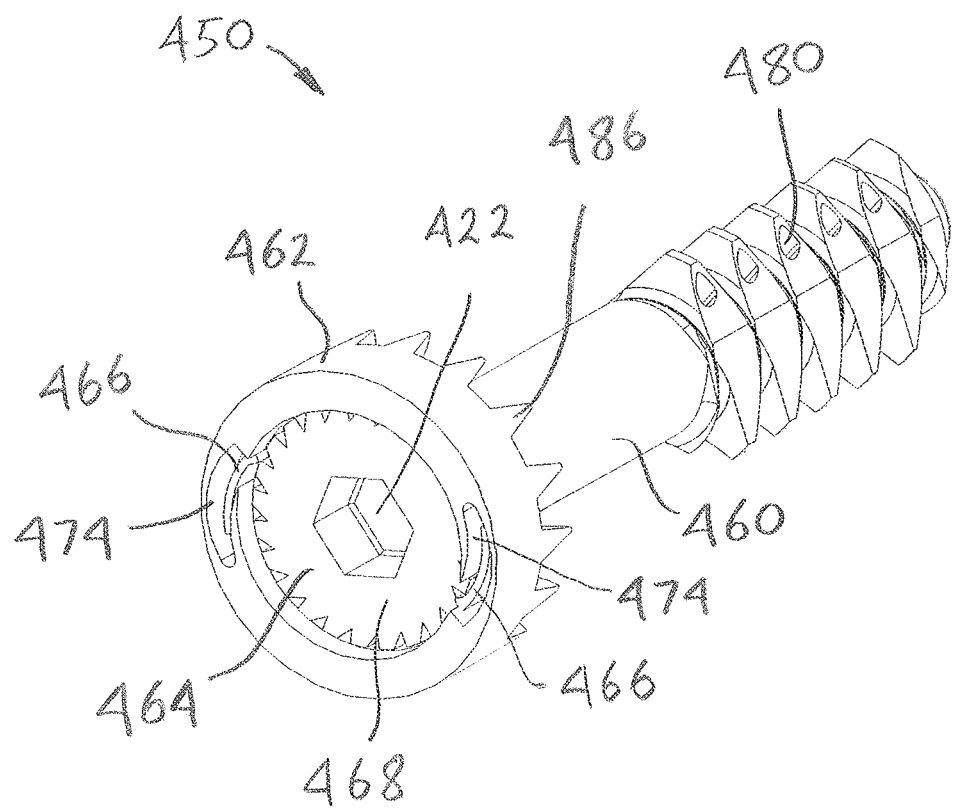
FIG. 23 is an opposite perspective view of the implant shown in FIG. 22.
Figure 24:
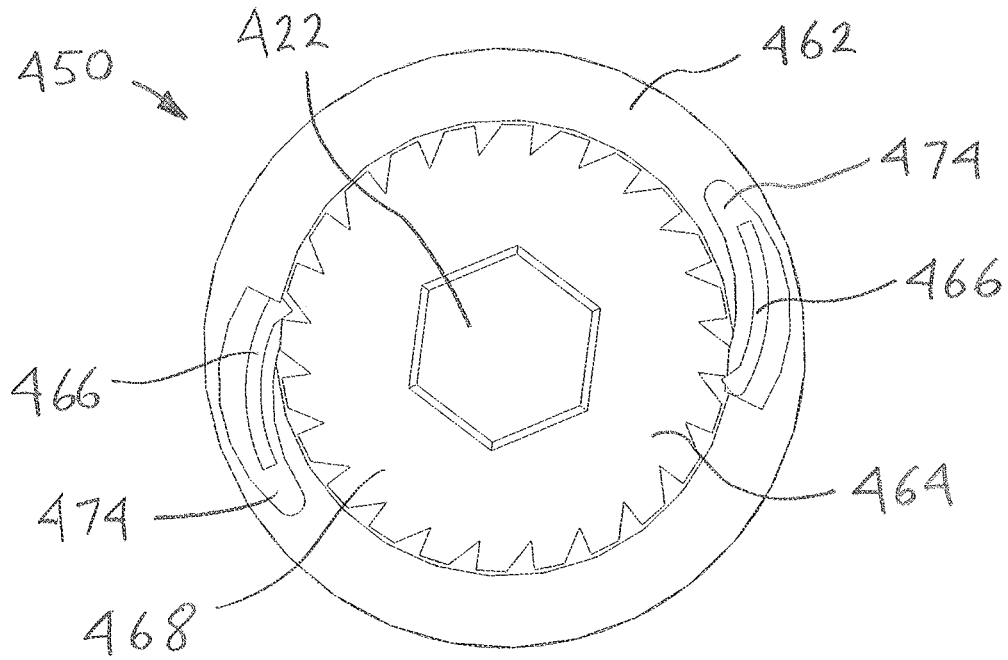
FIG. 24 is a proximal end view of the implant shown in FIG. 22.
Figure 25:
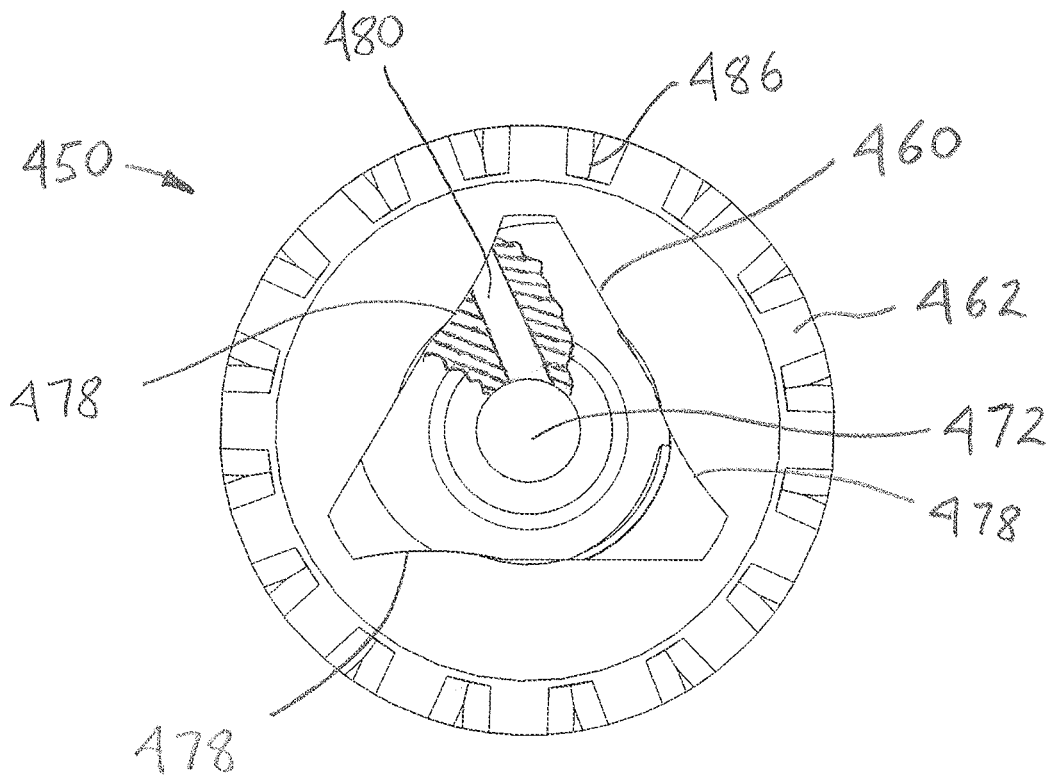
FIG. 25 is a distal end view of the implant shown in FIG. 22.
Figure 26:
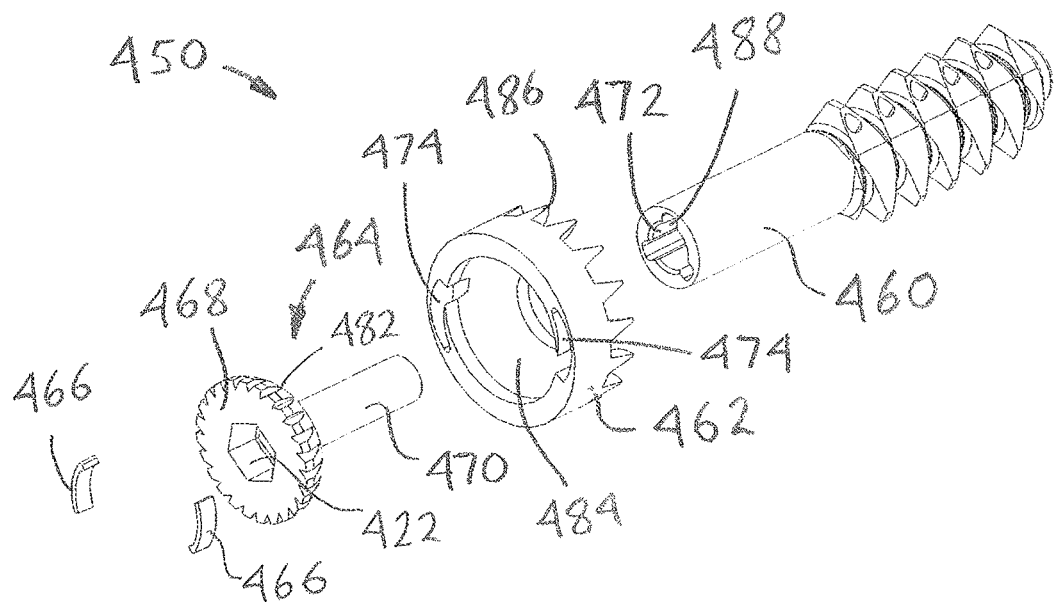
FIG. 26 is a perspective exploded view of the implant shown in FIG. 22.

Referring to FIGS. 22-27, another exemplary embodiment of a threaded implant system constructed according to aspects of the present disclosure is shown. As best seen in FIG. 26, implant 450 comprises a main body 460, a proximal screw cap 462, a proximal screw 464, and a pair of rotation stops 466. Proximal screw 464 comprises a head portion 468 and a shaft portion 470. Shaft portion 470 may be provided with external threads (not shown) for threadably engaging with internal threads (not shown) located in the proximal end of central bore 472 which passes through main body 460. When implant 450 is assembled (as best seen in FIGS. 22 and 23), proximal screw cap 462 is captivated between head portion 468 of proximal screw 464 and the proximal end of main body 460. Rotation stops 466 are recessed within curved slots 474 in proximal screw cap 462 (as best seen in FIGS. 23 and 24) such that they prevent or inhibit counter-clockwise rotation of proximal screw head portion 468 relative to proximal screw cap 462.

Figure 27:
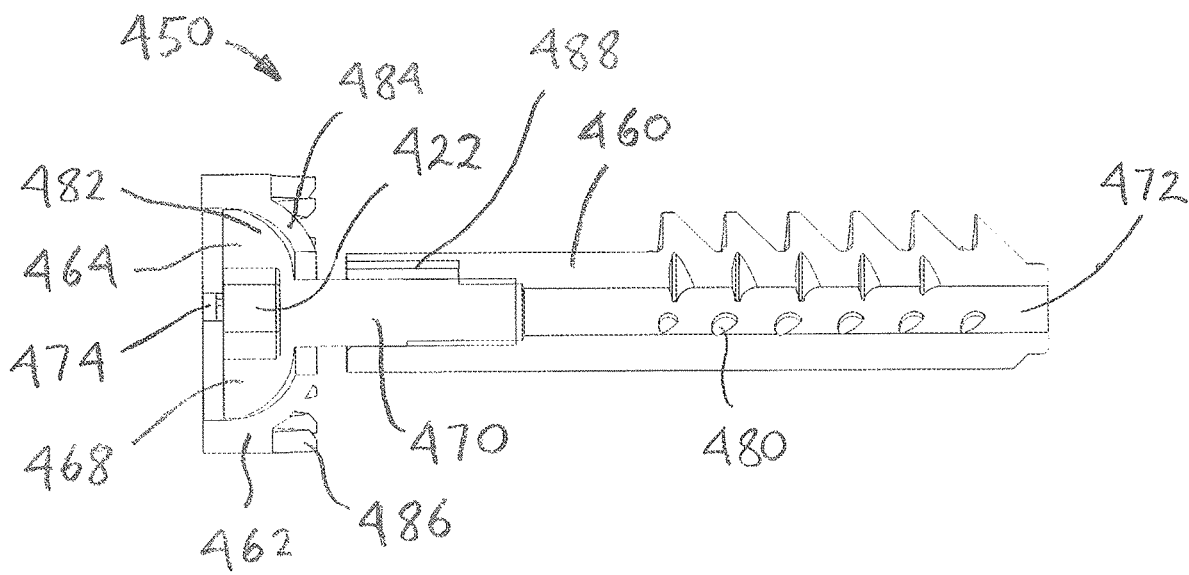
FIG. 27 is a side elevation exploded view of the implant shown in FIG. 22.

Referring to FIG. 22, the distal end of implant 450 may be provided with threads 476 configured to engage with a bone segment. In this embodiment, as best seen in FIG. 27, the threads 476 have a non-symmetrical longitudinal cross-section that has a saw-tooth pattern. More specifically, the proximal sides of the threads extend in a radial direction (perpendicular to the central axis of implant 450) while the distal sides of the threads are angled relative to the central axis. One advantage to this configuration is that it provides a higher pullout force when implanted in bone. It can also be seen in FIG. 27 that threads 476 get progressively wider as they extend proximally (i.e. the thread peaks get wider and the roots or valleys get narrower.) This arrangement allows for the more proximal threads to press against the adjacent bone grooves more than they otherwise would. The entire threaded area is constantly cutting into un-cut bone and allows the threads to create continuous compression into the bone during advancement.

As best seen in FIG. 25, the threads 476 have a transverse cross-section that is generally triangular in shape. A scoop, divot or hook shape 478 may be provided on the leading edge (when rotating in an insertion direction) of each apex of the triangular-shaped threads. A lateral bore 480 may also be provided to connect each scoop 478 or leading edge with central bore 472. The lateral bores 480, in conjunction with the scoops 478 if provided, serve to harvest bone chips or fragments (not shown) as implant 450 is threaded into place. Bone chips may pass through lateral bores 480 and into central bore 472 where they may accumulate. The bone chips may then be removed through the proximal end of central bore 472 and manually reintroduced around the implant, may be forced out the distal end of the implant with a tamper, pushed back out of lateral bores 480 once implant 450 is in the desired position, and/or may be left in place to promote bony ingrowth into implant 450.

Referring to FIGS. 26 and 27, the proximal side of head portion 468 of proximal screw 464 may be provided with a hexagonally shaped socket 422 for receiving a drive tool (not shown) when implant 450 is being inserted or removed. The distal side of head portion 468 may be provided with a curved, convex portion 482 configured to mate with a curved, concave portion 484 located on proximal screw cap 462. The circumference of the distal side of proximal screw cap 462 may be provided with a series of teeth 486 configured to bite into bone. With this arrangement, proximal screw cap 462 may freely pivot in two dimensions relative to proximal screw 464 so that most or all of the teeth 486 of screw cap 462 can engage with an outer surface of a bone segment when implant 450 is implanted therein, particularly when implant 450 is implanted in an orientation that is not orthogonal to the outer surface of the bone.

In this exemplary embodiment, main body 460 is implanted first without proximal screw cap 462 or proximal screw cap 464. The implant site may be prepared in a manner similar to those of previously described embodiments. A three-lobed driver tool (not shown) may be inserted into a mating three-lobe receptacle 488 (shown in FIG. 26) located at the proximal end of main body 460. Main body 460 may then be threaded into the bone to a desired height, for example, such that the proximal end of main body 460 is just below the outer surface of the bone. The driver tool is then removed from main body 460. Bone chips may then be packed into or moved inside central bore 472. Proximal screw cap 462 may then be placed over the implant bore or over the proximal screw 464, and the distal end of proximal screw 464 may be threaded into the proximal end of main body 460. A hexagonal driver tool (not shown) may be used to tighten proximal screw cap 462 against the outer surface of the bone. Rotation stops 466 inhibit proximal screw 464 from backing out, as previously described. In some embodiments, rotation stops 466 may be removed from proximal screw cap 462 after implantation to allow proximal screw 468 to be rotated in the opposite direction to remove implant 450.

In some embodiments (not shown), a compression spring may be provided between the proximal screw head or proximal screw cap and the proximal bone surface to maintain compression force on the joint and/or to inhibit the implant from backing out of the bone.

In any of the previously described embodiments, various thread profiles may be utilized. For example, a buttress, V, square, multi start, tapered (root and width), variable pitch, or other thread profile may be used. In some designs, the ISO 5835 standard from the American National Standards Institute (ANSI) may be used for guidance. Thread profiles may be designed to reduce stress concentrations. Variable thread depths may be used.

Materials that may be used to form the implants include: titanium alloy, stainless steel, ceramic, other alloys, polymers, and bone. In some embodiments, the implant or portions of the implant are additively manufactured. Porosity, fenestrations, nano tubes, nano surface treatments, hydroxyapatite, drug elution, bioactive and anti-microbial (e.g. silver) materials, coatings and/or treatments may be used to encourage bone growth and/or deliver therapeutic benefits. Porosity may vary radially, longitudinally, and/or in other manners. The implants may include expandable sections and may include a modular design.

The implants disclosed herein may be provided in a various incremental lengths to match various anatomies. In some implementations, the lengths range from 30 to 160 mm. In some implementations, various incremental diameters may be provided, such as 6 to 18 mm. In some implementations, the thread pitch is 1.5 to 10 mm. In some implementations, the pore size of some or all of the implant is 250 to 1000 microns. In some implementations, the porosity is 50 to 80%.

In some implementations, a threaded proximal portion configured to engage the ilium is 10 to 15 mm long, a triangular middle portion without threads is 10-15 mm long, and a distal threaded portion configured to engage the sacrum is provided in various lengths, depending on the anatomy of the particular implant site.

In any of the previously described embodiments, the external threads may get progressively wider as they extend proximally. This arrangement allows for the more proximal threads to press against the adjacent bone grooves more than they otherwise would to provide a tighter fit of the implant against the bone.

In some embodiments, the implants disclosed herein are specifically designed to accommodate four or five zones of the sacroiliac joint. These zones can include: 1) the lateral iliac wall; 2) the ilium; 3) the SI joint itself; 4) the sacral ala; and 5) sacral vertebral body. For example, the implant design may include 1) a mechanism to lock against the lateral iliac wall (such as a series of teeth 486 on a proximal head as previously described), 2) a finer thread configured to engage the ilium, 3) fenestrations configured to be located inside the SI joint itself when the device is implanted to promote bone ingrowth and/or deliver biologics, 4) a course thread for the ala, and 5) possibly a fine thread for the sacral body. Other suitable features may also be provided and configured for each of the zones, particularly the first four zones.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present disclosure.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the disclosure as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the disclosure as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An elongated threaded implant sized and configured for implantation in a sacroiliac joint of a patient, comprising:
    an internal support extending axially from a proximal end of the threaded implant to a distal end of the implant;
    an external thread extending radially outward relative to the internal support and extending axially along a length of the implant; and
    a porous infill disposed in a helical configuration about an implant axis between the external thread such that the porous infill forms a root diameter of the external thread,
        the porous infill comprising a plurality of pores sized to provide for one or more of bony on-growth, ingrowth or through-growth,
        the porous infill comprising a plurality of breaks in the helical configuration,
    wherein the plurality of breaks are in a helical configuration that is different than the helical configuration of the porous infill between the external thread,
    wherein a path defined by the helical configuration of the plurality of breaks is void of the porous infill,
    wherein the path has a pitch that is at least eight times a pitch of the helical configuration of the porous infill between the external thread, and
    wherein the internal support, the external thread, and the helically configured porous infill are manufactured from the same material, and are manufactured together, along with the helically configured plurality of breaks in the porous infill, during the same additive manufacturing process.

2. The threaded implant of claim 1, wherein the helically configured porous infill comprises a plurality of connected segments.

3. The threaded implant of claim 1, further comprising a through bore extending along a central axis of the threaded implant.

4. The threaded implant of claim 1, wherein the helically configured porous infill is at least 20% more porous than the external thread.

5. An elongated threaded implant sized and configured for implantation in a sacroiliac joint of a patient, comprising:
    an internal support extending axially from a proximal end of the threaded implant to a distal end of the implant;
    an external thread extending radially outward relative to the internal support and extending axially along a length of the implant; and
    a scaffolding disposed in a helical configuration about an implant axis between the external thread such that the scaffolding forms a root diameter of the external thread,
        the scaffolding comprising a plurality of pores sized to provide for one or more of bony on-growth, ingrowth or through-growth,
        the scaffolding comprising a plurality of breaks in the helical configuration,
    wherein the plurality of breaks are in a helical configuration that is different than the helical configuration of the scaffolding between the external thread, wherein a path defined by the helical configuration of the plurality of breaks is void of the scaffolding, wherein the path has a pitch that is at least eight times a pitch of the helical configuration of the scaffolding between the external thread, and wherein the internal support, the external thread, and the helically configured scaffolding are manufactured from the same material, and are manufactured together, along with the helically configured plurality of breaks in the scaffolding, during the same additive manufacturing process.

6. The threaded implant of claim 5, wherein the helically configured scaffolding comprises a plurality of connected segments.

7. The threaded implant of claim 5, further comprising a through bore extending along a central axis of the threaded implant.

8. The threaded implant of claim 5, wherein the helically configured scaffolding is at least 20% more porous than the external thread.

* * * * *